(12) United States Patent
Yoshikawa

(10) Patent No.: US 10,145,794 B2
(45) Date of Patent: Dec. 4, 2018

(54) CELL INFORMATION OBTAINING METHOD AND CELL INFORMATION OBTAINING APPARATUS

(71) Applicant: Sysmex Corporation, Kobe-shi, Hyogo (JP)

(72) Inventor: Keiko Yoshikawa, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 104 days.

(21) Appl. No.: 15/335,719

(22) Filed: Oct. 27, 2016

(65) Prior Publication Data

US 2017/0122869 A1 May 4, 2017

(30) Foreign Application Priority Data

Oct. 30, 2015 (JP) .................. 2015-215201
Jul. 25, 2016 (JP) .................. 2016-145835

(51) Int. Cl.

| | |
|---|---|
| *G01N 21/64* | (2006.01) |
| *G01N 21/05* | (2006.01) |
| *G01N 33/68* | (2006.01) |
| *C12Q 1/68* | (2018.01) |
| *G01N 15/14* | (2006.01) |
| *G01N 33/50* | (2006.01) |
| *G01N 33/58* | (2006.01) |
| *C12Q 1/6841* | (2018.01) |

(Continued)

(52) U.S. Cl.
CPC ....... *G01N 21/6428* (2013.01); *C12Q 1/6841* (2013.01); *G01N 15/147* (2013.01); *G01N 15/1434* (2013.01); *G01N 15/1468* (2013.01); *G01N 15/1475* (2013.01); *G01N 21/05* (2013.01); *G01N 21/6458* (2013.01); *G01N 33/5035* (2013.01); *G01N 33/582* (2013.01); *G01N 33/6875* (2013.01); *G01N 2015/1006* (2013.01); *G01N 2015/144* (2013.01); *G01N 2021/6421* (2013.01); *G01N 2021/6441* (2013.01)

(58) Field of Classification Search
CPC ......... C12Q 1/6841; G01N 2021/6441; G01N 21/05; G01N 21/6428; G01N 33/6875
See application file for complete search history.

(56) References Cited

U.S. PATENT DOCUMENTS

| | | | |
|---|---|---|---|
| 5,528,045 A | 6/1996 | Hoffman et al. | |
| 2004/0101912 A1* | 5/2004 | Rubin | ............ B82Y 5/00 435/7.2 |

(Continued)

FOREIGN PATENT DOCUMENTS

| | | |
|---|---|---|
| CN | 1653332 A | 8/2005 |
| CN | 1675551 A | 9/2005 |

(Continued)

*Primary Examiner* — Jennifer Wecker
(74) *Attorney, Agent, or Firm* — Brinks Gilson & Lione

(57) ABSTRACT

A cell information obtaining method comprises causing a plurality of fluorescent substances having different fluorescence wavelengths from each other to be bound to a test substance contained in a cell, applying light to the cell to cause fluorescences having different wavelengths and intensities to be generated from the plurality of fluorescent substances, and obtaining a first fluorescence information and a second fluorescence information on the basis of the generated fluorescences.

19 Claims, 23 Drawing Sheets

(51) Int. Cl.
*G02B 1/00* (2006.01)
*G01N 15/10* (2006.01)

(56) References Cited

U.S. PATENT DOCUMENTS

| | | | |
|---|---|---|---|
| 2010/0034453 A1 | 2/2010 | Lynch | |
| 2011/0017923 A1* | 1/2011 | Kubo | A61B 1/00009 |
| | | | 250/458.1 |
| 2011/0278471 A1* | 11/2011 | Hoshishima | G01N 15/1429 |
| | | | 250/459.1 |
| 2012/0029831 A1* | 2/2012 | Hoshishima | G01N 15/147 |
| | | | 702/19 |
| 2015/0132766 A1 | 5/2015 | Yasuda et al. | |

FOREIGN PATENT DOCUMENTS

| | | |
|---|---|---|
| CN | 1688717 A | 10/2005 |
| CN | 102439416 A | 5/2012 |
| JP | 2002-508504 A | 3/2002 |
| JP | 2002-189027 A | 7/2002 |
| WO | WO 00/79241 A2 | 12/2000 |
| WO | WO 2005/098430 A2 | 10/2005 |
| WO | WO 2010/045949 A2 | 4/2010 |

* cited by examiner

EMBODIMENT 2

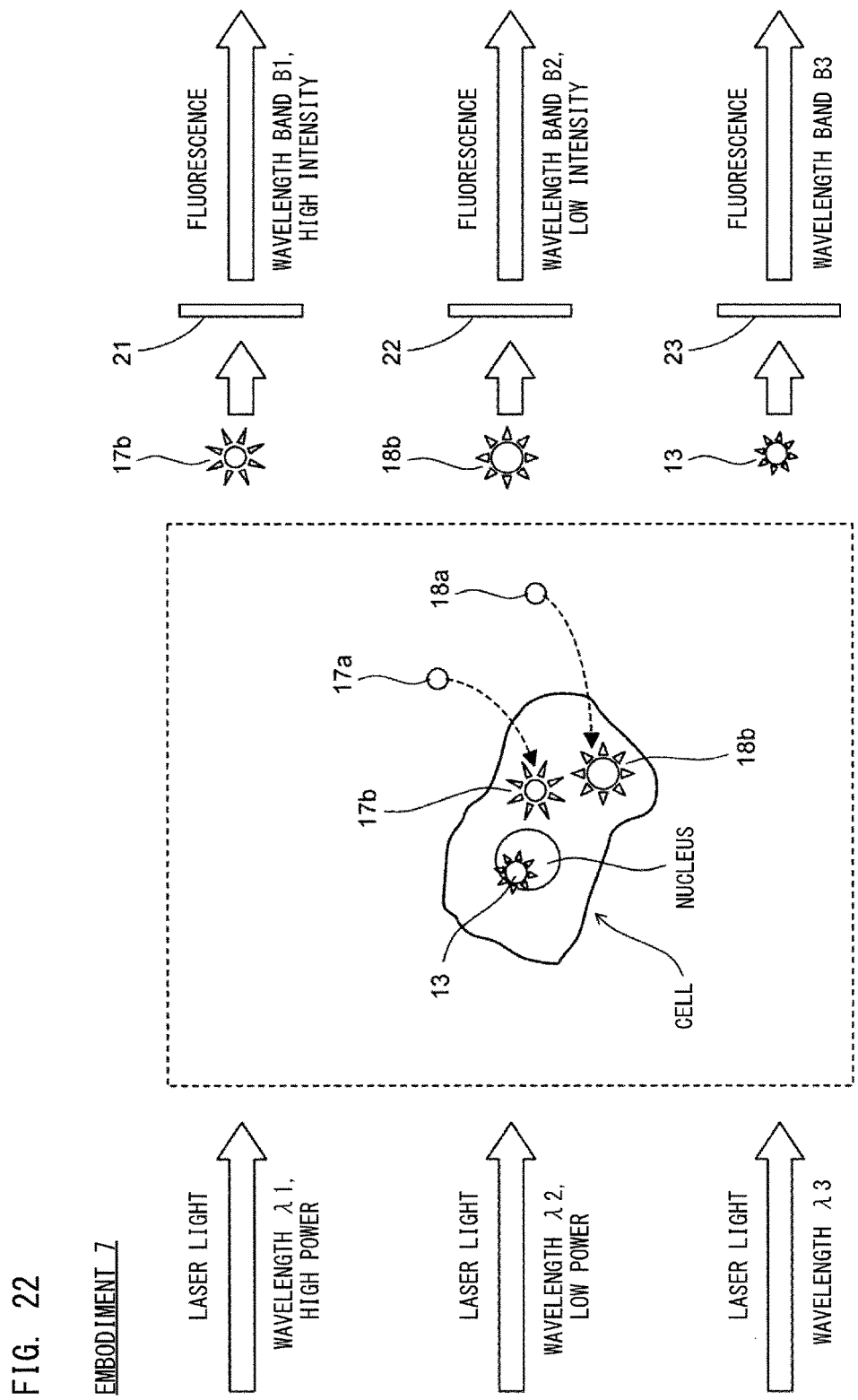

CELL INFORMATION OBTAINING METHOD AND CELL INFORMATION OBTAINING APPARATUS

CROSS REFERENCE TO RELATED APPLICATIONS

This application claims priority from prior Japanese Patent Application No. 2015-215201, filed on Oct. 30, 2015, entitled "CELL INFORMATION OBTAINING METHOD AND CELL INFORMATION OBTAINING APPARATUS" and prior Japanese Patent Application No. 2016-145835, filed on Jul. 25, 2016, entitled "CELL INFORMATION OBTAINING METHOD AND CELL INFORMATION OBTAINING APPARATUS", the entire content of which is incorporated herein by reference.

FIELD OF THE INVENTION

The present invention relates to cell information obtaining methods and cell information obtaining apparatuses.

BACKGROUND

Various biological phenomena including cell proliferation and cell differentiation involve localization of various molecules such as a protein, mRNA, and microRNA in a cell. Analysis of localization of various molecules in a cell is expected to lead to elucidation of many biological phenomena, including analysis of molecule functions, analysis of interaction between proteins, analysis of signal transduction pathways, and the like.

International Publication WO 2005/098430 discloses a method for analyzing localization of molecules in a cell by use of a fluorescence microscope and an imaging flow cytometer.

Even when cells are of the same kind derived from the same origin, the individual cells are diverse. Thus, for example, some sells have specific molecules localized in a specific site as shown in FIG. 23A, and other cells have specific molecules localized at another site as shown in FIG. 23B. Moreover, for example, in some cases, due to various factors, the amount of molecules is not uniform between cells as shown in FIG. 23C. The inventor has found that, when information is obtained from molecules having diverse distributions and amounts in cells, the obtained results are varied. Thus, a technique is desired that allows accurate analysis of molecules having diverse distributions and amounts in cells.

SUMMARY OF THE INVENTION

The scope of the present invention is defined solely by the appended claims, and is not affected to any degree by the statements within this summary.

A first mode of the present invention relates to a cell information obtaining method. The cell information obtaining method according to this mode includes: causing a plurality of fluorescent substances having different fluorescence wavelengths from each other to be bound to a test substance contained in a cell; applying light to the cell to cause fluorescences having different wavelengths and intensities to be generated from the plurality of fluorescent substances; and obtaining a first fluorescence information and a second fluorescence information on the basis of the generated fluorescences.

In the cell information obtaining method according to this mode, a "plurality of fluorescent substances having different fluorescence wavelengths from each other" means that, when light is applied, a plurality of fluorescent substances respectively emit fluorescences having different wavelengths from each other. In order to cause fluorescences having different wavelengths and intensities to be generated from a plurality of fluorescent substances, in a case where, for example, the wavelengths of excitation light are respectively different for the plurality of fluorescent substances, a plurality of lights having different wavelengths and intensities are applied to a cell. The fluorescence information is an image based on fluorescence, for example. "To cause a plurality of fluorescent substances to be bound to a test substance" means that: the plurality of fluorescent substances may not necessarily be bound to all the test substance molecules of the same kind contained in a cell; and it is sufficient that the plurality of fluorescent substances are specifically bound to at least some of the test substance molecules of the same kind.

A second mode of the present invention relates to a cell information obtaining method. The cell information obtaining method according to this mode includes: bringing a substrate into contact with a test substance contained in a cell, to cause a plurality of fluorescent substances having different fluorescence wavelengths from each other to be generated; applying light to the cell to cause fluorescences having different wavelengths and intensities to be generated from the plurality of fluorescent substances; and obtaining a first fluorescence information and a second fluorescence information on the basis of the generated fluorescences.

A third mode of the present invention relates to a cell information obtaining method. The cell information obtaining method according to this mode includes: causing a fluorescent substance to be bound to a test substance contained in a cell; applying light to the cell to cause a fluorescence to be generated from the fluorescent substance; obtaining, from the generated fluorescence, a plurality of fluorescences having different wavelengths and intensities; obtaining a first fluorescence information and a second fluorescence information on the basis of the obtained fluorescences; and identifying a distribution state of the test substance in the cell on the basis of the first fluorescence information and the second fluorescence information.

A fourth mode of the present invention relates to a cell information obtaining method. The cell information obtaining method according to this mode includes: bringing a substrate into contact with a test substance contained in a cell, to cause a fluorescent substance to be generated; applying light to the cell to cause a fluorescence to be generated from the fluorescent substance; obtaining a plurality of fluorescences having different wavelengths and intensities from the generated fluorescence; obtaining a first fluorescence information and a second fluorescence information on the basis of the obtained fluorescences; and identifying a distribution state of the test substance in the cell on the basis of the first fluorescence information and the second fluorescence information.

A fifth mode of the present invention relates to a cell information obtaining apparatus. The cell information obtaining apparatus according to this mode includes: a light application unit configured to apply light to a cell containing a test substance to which a plurality of fluorescent substances having different fluorescence wavelengths from each other are bound, thereby to cause fluorescences having different wavelengths and intensities to be generated from the plurality of fluorescent substances; a light receiver configured to receive the fluorescences generated from the plurality of fluorescent substances; and an obtaining section configured to obtain a first fluorescence information and a second fluorescence information on the basis of the fluorescences having different intensities.

A sixth mode of the present invention relates to a cell information obtaining apparatus. The cell information obtaining apparatus according to this mode includes: a light application unit configured to apply light to a cell containing a test substance to which a fluorescent substance is bound, thereby to cause a fluorescence to be generated from the fluorescent substance; a light receiver configured to receive a plurality of fluorescences having different wavelengths and intensities generated from the fluorescent substance; an obtaining section configured to obtain a first fluorescence information and a second fluorescence information on the basis of the received plurality of fluorescences; and an analysis section configured to identify a distribution state of the test substance in the cell on the basis of the first fluorescence information and the second fluorescence information.

A seventh mode of the present invention relates to a cell information obtaining apparatus. The cell information obtaining apparatus according to this mode includes: a light application unit configured to apply light to a cell containing a test substance, which has been brought into contact with a substrate to cause a fluorescent substance to be generated, thereby to cause a fluorescence to be generated from the fluorescent substance; a light receiver configured to receive a plurality of fluorescences having different wavelengths and intensities generated from the fluorescent substance; an obtaining section configured to obtain a first fluorescence information and a second fluorescence information on the basis of the received plurality of fluorescences; and an analysis section configured to identify a distribution state of the test substance in the cell on the basis of the first fluorescence information and the second fluorescence information.

BRIEF DESCRIPTION OF THE DRAWINGS

FIG. 22 shows the outline of how to obtain fluorescence according to Embodiment 7.

DETAILED DESCRIPTION OF THE PREFERRED EMBODIMENTS

Embodiment 1

Embodiment 1 is realized by a cell information obtaining method in which: a plurality of fluorescent substances having different fluorescence wavelengths from each other are caused to be bound to a test substance contained in a cell; and the localization state of the test substance is identified on the basis of a plurality of fluorescences respectively generated from the fluorescent substances. In Embodiment 1, the test substance is NF-κB. NF-κB being a transcription factor is considered to be present in the cytoplasm in a state of a complex with IκB, and to move into the nucleus due to degradation of IκB caused by various stimuli. In Embodiment 1, NF-κB being the test substance is specifically labeled with a fluorescent substance, and on the basis of the fluorescence from the fluorescent substance, whether NF-κB is present in the cytoplasm or the nucleus is determined. It should be noted that the test substance may be a molecule or a protein other than NF-κB. For example, the test substance may be a transcription factor other than NF-κB, and may be, for example, STAT (Signal Transducer and Activator of Transcription), NFAT (nuclear factor of activated T cells), or HIF (hypoxia-inducible factor). Alternatively, the test substance may be mRNA or microRNA. "A plurality of fluorescent substances are caused to be bound to a test substance" means that: the plurality of fluorescent substances may not necessarily be bound to all the test substance molecules of the same kind contained in a cell; and it is sufficient that the plurality of fluorescent substances are specifically bound to at least some of the test substance molecules of the same kind. Furthermore, the identification of the localization state is not limited to identification of whether the test substance is localized in the nucleus or localized in the cytoplasm. For example, in the case of a protruded shape like a neuron, whether the test substance is localized at the tip of the protrusion may be identified.

Figure 1:
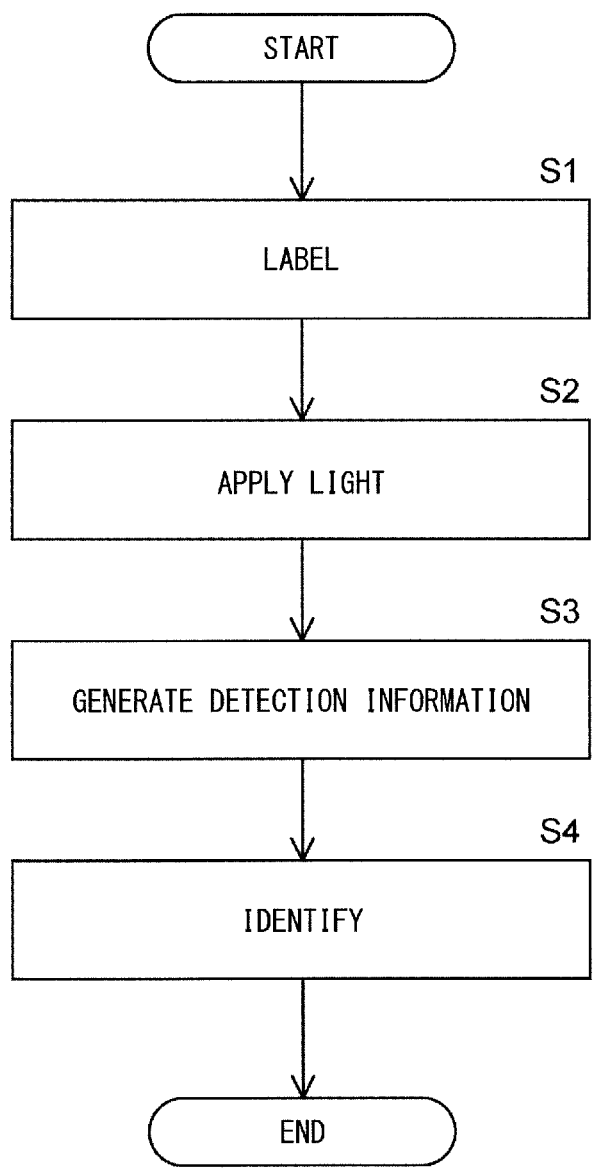
FIG. 1 is a flow chart showing a cell information obtaining method according to Embodiment 1.

As shown in FIG. 1, the cell information obtaining method includes steps S1 to S4. In the following, a case will be described in which an operator executes the cell information obtaining method shown in FIG. 1, by using a flow cytometer capable of taking fluorescence images and a processing apparatus capable of analyzing the taken images. Each step shown in FIG. 1 may be executed as a process performed by a cell information obtaining apparatus. The configuration and the process for a case where the cell information obtaining apparatus performs each step in FIG. 1 will be described with reference to FIG. 5 and thereafter.

Figure 2:
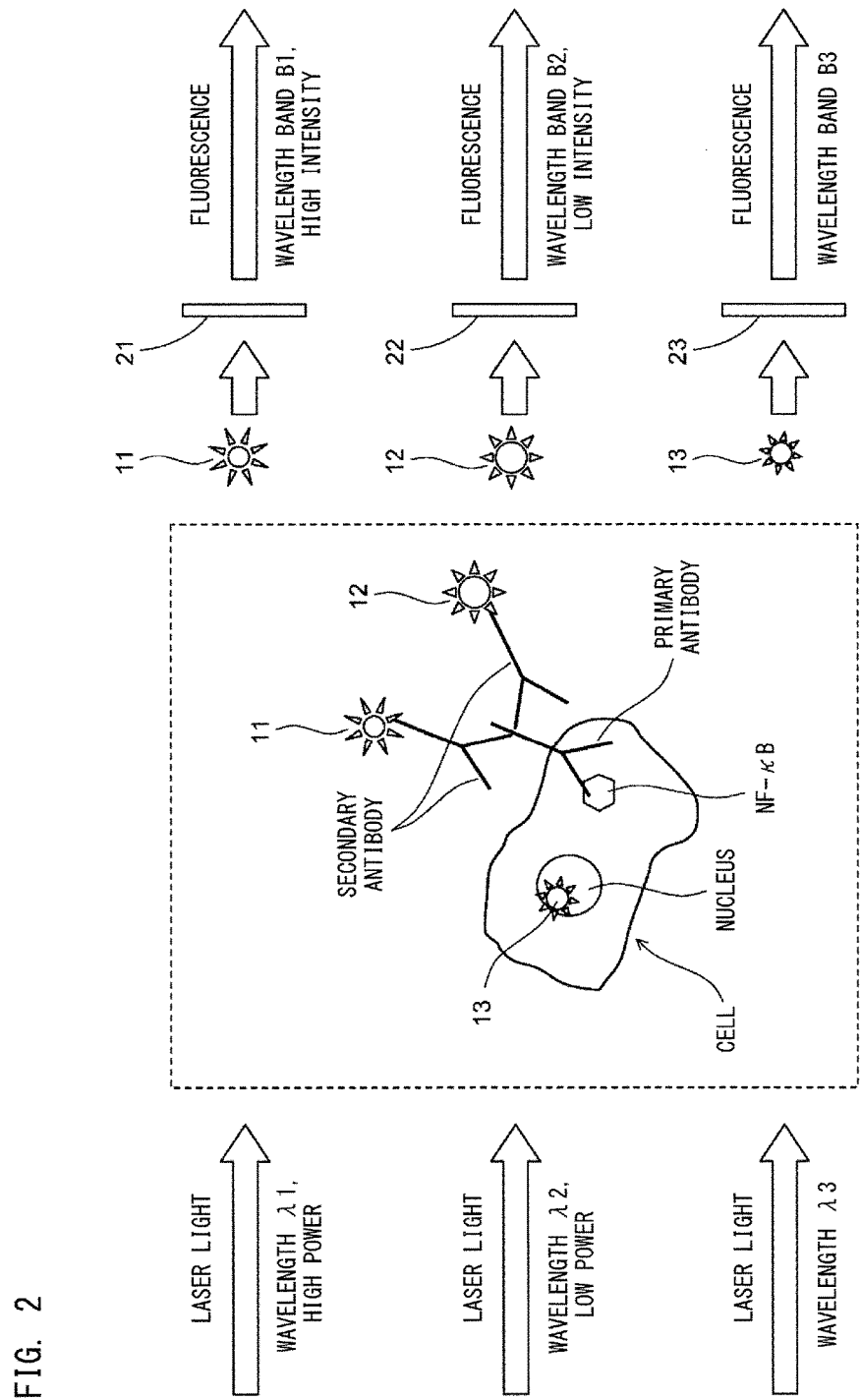
FIG. 2 shows the outline of how to obtain fluorescence according to Embodiment 1.

In step S1, the operator labels NF-κB contained in cells collected from a subject, with fluorescent substances 11 and 12 having different fluorescence wavelengths from each other. For example, as shown in FIG. 2, the fluorescent substances 11 and 12 are bound to NF-κB contained in a cell, via a primary antibody and a secondary antibody. The fluorescent substances 11 and 12 may be bound to NF-κB via a plurality of the primary antibodies, or may be bound to NF-κB via a part of the antibody or the entirety of the antibody. In addition, in step S1, the operator labels the nucleus contained in the cell with a fluorescent substance 13 having a fluorescence wavelength different from those of the fluorescent substances 11 and 12.

The fluorescent substances 11, 12, and 13 are each a fluorescent dye. The fluorescent substances 11, 12, and 13 are respectively configured to excite fluorescences having different wavelength bands from each other, upon being irradiated with lights having wavelengths $\lambda 1$, $\lambda 2$, and $\lambda 3$. That is, the wavelengths of lights for exciting fluorescences from the fluorescent substances 11 to 13 are set to be different from each other. In this manner, a sample is prepared in step S1. It should be noted that, when the test substance is mRNA or microRNA, such a fluorescent substances is bound to the test substance via a nucleic acid probe.

In step S2, the operator drives a flow cytometer. Then, the operator causes the sample, which contains the cells labeled with the fluorescent substances 11 to 13, to flow in a flow cell. Then, the operator causes lights respectively having wavelengths $\lambda 1$ to $\lambda 3$ to be applied to each cell flowing in the flow cell, thereby causing fluorescences to be generated from the fluorescent substances 11 to 13.

As shown in FIG. 2, when laser lights respectively having wavelengths $\lambda 1$ to $\lambda 3$ are applied to the cell, fluorescences having different wavelength bands are generated from the fluorescent substances 11 to 13, respectively. A filter member 21 allows fluorescence having a wavelength band B1 and having been generated from the fluorescent substance 11 to pass therethrough, and blocks light other than light having the wavelength band B1. The fluorescence having the wavelength band B1 and having been generated from the fluorescent substance 11 is separated by the filter member 21. A filter member 22 allows fluorescence having a wavelength band B2 and having been generated from the fluorescent substance 12 to pass therethrough, and blocks light other than light having the wavelength band B2. The fluorescence having the wavelength band B2 and having been generated from the fluorescent substance 12 is separated by the filter member 22. A filter member 23 allows fluorescence having a wavelength band B3 and having been generated from the fluorescent substance 13 to pass therethrough, and blocks light other than light having the wavelength band B3. The fluorescence having the wavelength band B3 and having been generated from the fluorescent substance 13 is separated by the filter member 23.

Here, the laser light having the wavelength $\lambda 1$ is applied to the cell at a high power, and the laser light having the wavelength $\lambda 2$ is applied to the cell at a low power. Since the laser light having the wavelength $\lambda 1$ is applied to the cell at a high power, the fluorescence having the wavelength band B1 and having passed through the filter member 21 has a high intensity. Since the laser light having the wavelength $\lambda 2$ is applied to the cell at a low power, the fluorescence having the wavelength band B2 and having passed through the filter member 22 has a low intensity.

In step S3, the processing apparatus obtains three pieces of fluorescence information for each cell, on the basis of fluorescences respectively generated from the fluorescent substances 11 to 13. The flow cytometer includes a configuration in which: fluorescences respectively having the wavelength bands B1 to B3 and having been separated by the filter members 21 to 23 are caused to form images, respectively, on a light receiver implemented by an image pickup device, thereby obtaining images based on the respective fluorescences. On the basis of image pickup signals outputted by the light receiver of the flow cytometer, the processing apparatus obtains, as the fluorescence information, an image based on the high intensity fluorescence having the wavelength band B1, an image based on the low intensity fluorescence having the wavelength band B2, and an image based on the fluorescence having the wavelength band B3.

Images of the fluorescences having the wavelength bands B1 to B3 may be individually taken by three light receivers, respectively, or may be taken by a single light receiver. When the fluorescences having the wavelength bands B1 to B3 are taken by a single light receiver, the optical system is configured such that the fluorescences having the wavelength bands B1 to B3 form respective images in different regions on the light receiving surface of the light receiver.

Figure 3:
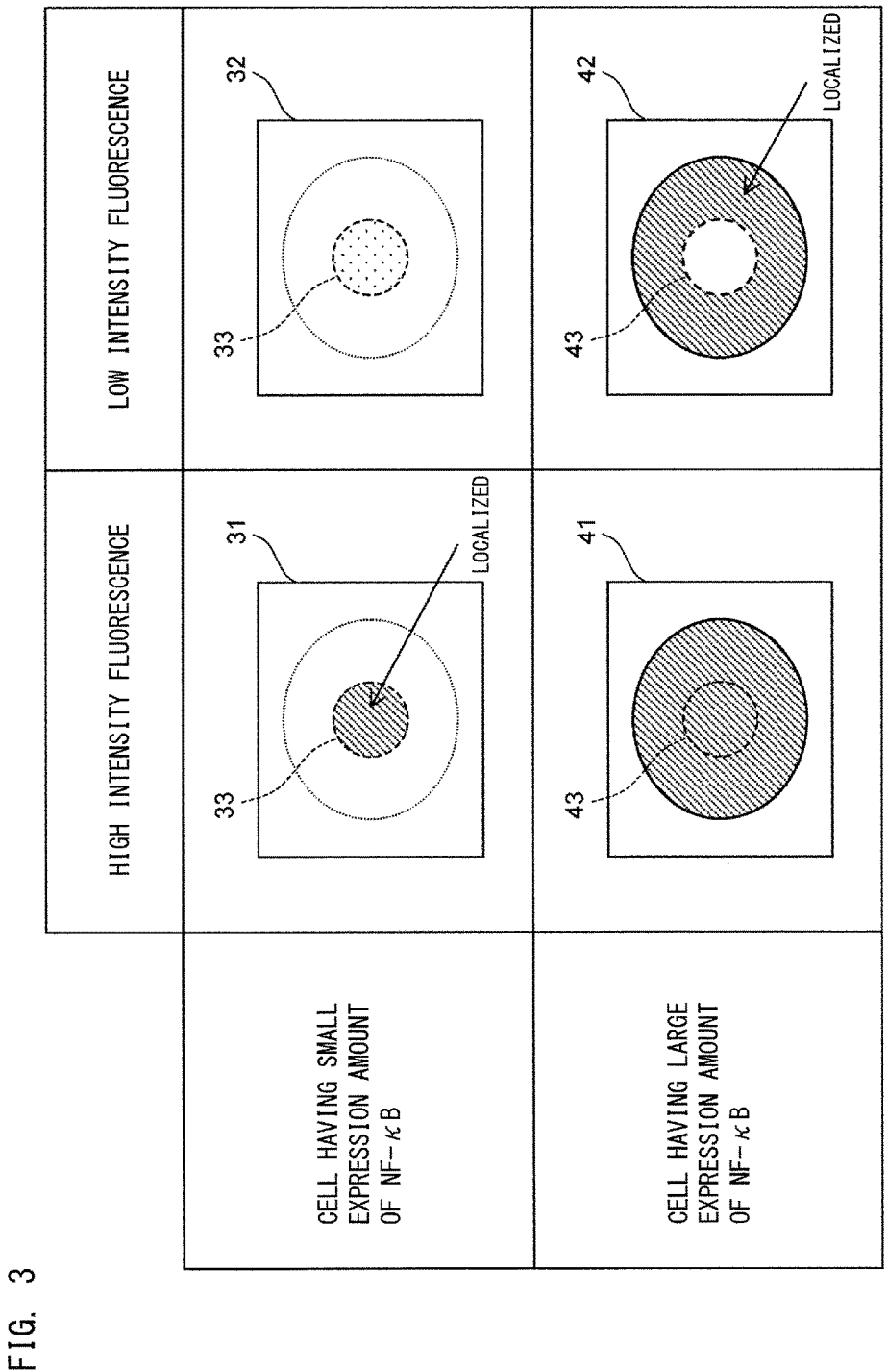
FIG. 3 is a conceptual diagram showing images obtained on the basis of high intensity fluorescence and low intensity fluorescence according to Embodiment 1.

As shown in FIG. 3, in the case of a cell where NF-κB is localized in the nucleus, images 31 and 32 are obtained in step S3, for example. The image 31 is based on the high intensity fluorescence having the wavelength band B1, and the image 32 is based on the low intensity fluorescence having the wavelength band B2. In each of the images 31 and 32, a region 33 where the nucleus is present is set. The region 33 is obtained from an image based on the fluorescence of the wavelength band B3, i.e., an image based on the fluorescence generated from the nucleus, the image having been generated simultaneously with the images 31 and 32.

In the case of a cell where NF-κB is localized in the cytoplasm, images 41 and 42 are obtained in step S3, for example. The image 41 is based on the high intensity fluorescence having the wavelength band B1, and the image 42 is based on the low intensity fluorescence having the wavelength band B2. Also in each of the images 41 and 42, a region 43 where the nucleus is present is set. The region 43 is obtained from an image based on the fluorescence having the wavelength band B3 and having been generated simultaneously with the images 41 and 42.

In the case of a cell having a small expression amount of NF-κB, with reference to the image 31, the intensity of the fluorescence is appropriate, and there is a difference in the fluorescence intensity between the nucleus and the cytoplasm. Thus, it is possible to identify that NF-κB is localized in the region 33 of the nucleus. Meanwhile, with reference to the image 32, the intensity of the fluorescence is too low, it is not possible to identify that NF-κB is localized in the region 33 of the nucleus. On the other hand, in the case of a cell having a large expression amount of NF-κB, with reference to the image 41, the intensity of the fluorescence is too high, and thus, no difference is observed in the fluorescence intensity between the nucleus and the cytoplasm. Thus, it is not possible to identify whether NF-κB is localized in the nucleus region 43 or the cytoplasm region which is larger than the nucleus region 43. Meanwhile, with reference to the image 42, the intensity of the fluorescence is appropriate, and there is a difference in the intensity between the nucleus and the cytoplasm. Thus, it is possible to identify that NF-κB is localized in the cytoplasm region which is larger than the nucleus region 43.

When NF-κB is localized in the cytoplasm, NF-κB is distributed in the cell in such a manner as to surround the nucleus. That is, when the cell is viewed in the image-taking direction, NF-κB is present also on the side nearer to the viewer relative to the nucleus. Thus, in the image 41 based on the high intensity fluorescence, strong fluorescence is generated also in the nucleus region due to the presence of NF-κB on the side nearer to the viewer relative to the nucleus. Thus, in the case of the image 41, appropriate identification on whether NF-κB is localized in the nucleus or localized in the cytoplasm is less likely to be realized. In contrast, in the case of the image 42 based on the low intensity fluorescence, although NF-κB that is present on the side nearer to the viewer relative to the nucleus causes fluorescence to be generated also in the nucleus region, the intensity of this fluorescence is low. Thus, in the case of the image 41, even when NF-κB is localized in the cytoplasm, the localization state can be appropriately identified.

When NF-κB is localized in the nucleus, although NF-κB is partially distributed in the cytoplasm, most of NF-κB is distributed in the nucleus. Thus, in the case of the image 31 based on the high intensity fluorescence, strong fluorescence is generated from NF-κB that is distributed in the nucleus. Thus, localization of NF-κB in the nucleus can be appropriately identified. On the other hand, in the case of the image 32 based on the low intensity fluorescence, since fluorescence from NF-κB that is distributed in the nucleus is too weak, appropriate identification on whether NF-κB is localized in the nucleus or localized in the cytoplasm is less likely to be realized.

As described above, depending on the amount and the distribution of NF-κB being a test substance in a cell, the appropriate intensity for identifying localization of NF-κB is different.

Therefore, the power of the laser light having the wavelength λ1 is set such that, in a cell where NF-κB is localized in the nucleus, localization of NF-κB in the nucleus can be appropriately identified as shown in the image 31. The power of the laser light having the wavelength λ2 is set such that, in a cell where NF-κB is localized in the cytoplasm, localization of NF-κB in the cytoplasm can be appropriately identified as shown in the image 42. Accordingly, in a cell as the target of the identification, whether NF-κB is localized in the nucleus or in the cytoplasm, it becomes possible to identify localization of NF-κB by using at least one of the two images.

With reference back to FIG. 1, in step S4, the operator identifies the distribution state of NF-κB being the test substance by referring to the image based on the high intensity fluorescence having the wavelength band B1 and the image based on the low intensity fluorescence having the wavelength band B2. Specifically, from the image based on the high intensity fluorescence having the wavelength band B1 and the image based on the low intensity fluorescence having the wavelength band B2, the operator selects an image which allows identification of the localization position of NF-κB. Then, on the basis of the selected image, the operator identifies whether NF-κB is localized in the nucleus or in the cytoplasm of the cell, i.e., the localization state. Instead of the localization state, the position at which the NF-κB is distributed, for example, the distribution range of the NF-κB in the cell, may be identified.

As described above, in Embodiment 1, through the adjustment of the two fluorescences generated from the fluorescent substances 11 and 12 labeling NF-κB, either one of the image based on the high intensity fluorescence and the image based on the low intensity fluorescence allows appropriate judgement on the localization of NF-κB. Accordingly, the operator can accurately analyze NF-κB having diverse distribution in the cell, on the basis of the two images. Specifically, it is possible to accurately identify the localization state of NF-κB in the cell, i.e., whether NF-κB is localized in the nucleus or in the cytoplasm.

In Embodiment 1, it is conceivable that: even when NF-κB is localized in the nucleus, if the amount of NF-κB is too large, the intensity of the fluorescence of the image 31 becomes too high; and thus, the intensity of the fluorescence of the image 32 is suitable. Even in such a case, by using the image 32 having the suitable fluorescence intensity, the localization of NF-κB in the nucleus can be determined. Similarly, it is also conceivable that: even when NF-κB is localized in the cytoplasm, the intensity of the fluorescence of the image 41 is suitable because the amount of NF-κB is small and the intensity of the fluorescence of the image 42 is too low. Also in such a case, by using the image 41 having the suitable fluorescence intensity, the localization of NF-κB in the cytoplasm can be identified. In this manner, according to Embodiment 1, on the basis of the two images, the localization state of NF-κB in the cell can be accurately identified irrespective of the amount of NF-κB.

Meanwhile, vascular endothelial cells detach from the inner wall of blood vessels and flow into blood. Detachment of vascular endothelial cells is caused not only by inflammatory stimuli but also by pressure change due to compression or the like. In vascular endothelial cells detached due to inflammatory stimuli, NF-κB is likely to be localized in the nucleus. In vascular endothelial cells detached due to stimuli other than inflammatory stimuli, NF-κB is less likely to be localized in the nucleus. According to Embodiment 1, localization of NF-κB can be accurately identified as described above, and thus, the detachment caused by inflammatory stimuli among those causes of detachment can be identified on the basis of whether NF-κB as the signaling molecule is localized in the nucleus. Thus, the presence/absence of activation of vascular endothelial cells can be determined. Accordingly, for example, it is possible to determine whether the detachment of vascular endothelial cells has been caused by compression at the time of blood collection, or caused by a factor such as a disease. This provides clinical significance.

An image having an intermediate intensity fluorescence may be obtained by using a middle-power laser light having a wavelength different from the wavelengths λ1 and λ2. That is, it may be configured such that: NF-κB is labeled with three fluorescent substances having different fluorescence wavelengths from each other; three laser lights are applied to each cell to cause fluorescences having different intensities to be generated from the three fluorescent substances, respectively; and images based on the respective fluorescences are obtained. With this configuration, by using the most appropriate image from among the three images having different fluorescence intensities, localization of NF-κB can be more accurately identified. Four or more levels may be employed for the intensity level of fluorescence to be generated from the test substance. Four or more images based on fluorescences respectively having four or more intensities may be obtained for each cell.

Further, in step S4, on the basis of the localization state per cell identified as above, the operator obtains the proportion of cells in each of which NF-κB is localized in a specific site among the cells contained in the sample. Specifically, when the number of cells for each of which NF-κB has been identified as being localized in the nucleus is defined as N1, and the number of cells for each of which NF-κB has been identified as being localized in the cytoplasm is defined as N2, the operator obtains a nuclear localization percentage and a cytoplasmic localization percentage according to the following formula. It should be noted that, in step S4, the operator may obtain a nuclear localization number and a cytoplasmic localization number, instead of the nuclear localization percentage and the cytoplasmic localization percentage.

Nuclear localization percentage=$\{N1/(N1+N2)\}\times 100$

Cytoplasmic localization percentage=$\{N2/(N1+N2)\}\times 100$

In step S2, an image of each fluorescence is obtained by use of the flow cytometer as described above, but not limited thereto, an image of each fluorescence may be obtained as the fluorescence information by use of a microscope. That is, by use of the microscope, an image based on high intensity fluorescence generated from the fluorescent substance 11, an image based on low intensity fluorescence generated from the fluorescent substance 12, and an image corresponding to the nucleus generated from the fluorescent substance 13 may be obtained.

Examination of Embodiment 1

Next, examination of Embodiment 1 performed by the inventor will be described.

1. Preparation

As the cells, human cardiac microvascular endothelial cells (HMVEC-C) (Lonza Cat No. CC-7030, Lot No. 0000296500 (P4)) were obtained. As the primary antibody, NF-κB p65 (D14E12) XP Rabbit mAb (Cell Signaling Technologies #8242S) was obtained. As the secondary antibody, Goat anti-Rabbit IgG (H+L) Secondary Antibody, Alexa Fluor 647 conjugate (Life technologies A-21245), and Goat anti-Rabbit IgG (H+L) Secondary Antibody, Alexa Fluor 488 conjugate (Life technologies A-11008) were obtained. To the secondary antibodies, Alexa Fluor 647 and Alexa Fluor 488 were bound, as the fluorescent dyes. As the nucleus staining dye, Cellstain Hoechst 33342 solution (DOjinDO H342) was obtained. Other than these, EGM-2MV Medium (Lonza Cat No. CC-3202), EGM-2MV SingleQuots Kit (Lonza Cat No. CC-3202), PBS pH7.4 (GIBCO Cat No. 10010-023), BSA (LAMPIRE Cat No. 7500805), PFA (WAKO Cat No. 160-16061), and TritonX100 (Nacalai Tesque Cat No. 35501-15) were obtained.

2. Reagent Preparation

Reagents other than FBS of EGM-2MV SingleQuots Kit were added to 500 mL of EGM-2MV Medium, and 100 mL of the mixture was taken into a sterilized bottle, to create a serum-free medium. To the remaining amount (400 mL) after the creation of the serum-free medium, 20 mL of FBS of SingleQuots Kit was added, to create a culture medium. Paraformaldehyde was dissolved in pH12 PBS so as to have a final concentration of 8% w/v, and then the pH was adjusted to 7.4. 1.5 g of BSA was added to and dissolved in PBS, and PBS was additionally added thereto to obtain 50 mL, whereby 3% BSA/PBS was prepared. 0.5 g of BSA was added to and dissolved in PBS, and PBS was additionally added thereto to obtain 50 mL, whereby 1% BSA/PBS was prepared. TritonX100 was adjusted with PBS so as to have a final concentration of 0.1% w/v.

3. Procedure

HMVEC-C cells were cultured in the EGM-2MV culture medium in accordance with a manufacturer-recommended protocol. Cells within six passages after the purchase thereof were used in this examination. The shelf life of the culture medium after opening was set to three weeks. For TNF-α-stimulated culture, the culture supernatant of about 70% confluent HMVEC-C cells was removed, and an EGM-2MV culture medium to which Recombinant Human TNF-alpha had been added so as to have a final concentration of 25 ng/mL was added. Then, the resultant mixture was left still for 1 hour in a 37° C. $CO^2$ incubator. The culture medium was removed with an electric pipette, with about 3 mL left, and the cells were detached with a scraper. 8% PFA/PBS was added by an amount equivalent to the collected suspension, and the resultant mixture was allowed to react at room temperature for 15 minutes. At room temperature, centrifugal separation was performed at 1000 rpm for 3 minutes. The cell pellet was washed with 1 mL of PBS twice. The supernatant was removed, and 1 mL of 0.1% Triton X-100/PBS was added. Then, the resultant mixture was allowed to react at room temperature for 15 minutes. At room temperature, centrifugal separation was performed at 1000 rpm for 3 minutes. The cells were washed with 1 mL of 1% BSA/PBS twice. The supernatant was removed and 1 mL of 3% BSA/PBS was added. Then, the resultant mixture was left still for 30 minutes at room temperature. 400 μL of the primary antibody diluted at a ratio of 1/1600 in 3% BSA/PBS was added. The resultant mixture was allowed to react at room temperature for 1 hour. At room temperature, centrifugal separation was performed at 1000 rpm for 3 minutes. The cells were washed with 1 mL of 1% BSA/PBS. 400 μL of the secondary antibody diluted at a ratio of 1/1000 in 3% BSA/PBS was added. The resultant mixture was allowed to react at room temperature for 30 minutes. The cells were washed with 1 mL of 1% BSA/PBS twice. The supernatant was removed and 50 μL of 1% BSA/PBS was added.

4. Detection by Flow Cytometer

As a flow cytometer that can obtain fluorescence images, ImageStreamX Mark II Imaging Flow Cytometer (Merck Millipore) was used. A sample prepared in accordance with the procedure 3 above was caused to flow in the flow cell of the flow cytometer. Laser lights respectively having wavelengths of 488 nm, 647 nm, and 405 nm were applied to the sample flowing in the flow cell. The laser lights having the wavelengths of 488 nm, 647 nm, and 405 nm respectively correspond to laser lights having the wavelengths λ1, λ2, and λ3 described above. The emission powers of the laser lights having the wavelengths of 488 nm, 647 nm, and 405 nm were set to 55 mW, 10 mW, and 120 mW, respectively. As a result of the application of the laser lights having the wavelengths 488 nm and 647 nm to the two kinds of fluorescent dyes labelling NF-κB, high intensity fluorescence and low intensity fluorescence were generated, respectively. As a result of the application of the laser light having the wavelength 405 nm to the nucleus staining dye, fluorescence was generated.

In the flow cytometer above, an image of the fluorescence generated due to the laser light having the wavelength of 488 nm was taken via a filter member having a transmission wavelength band of 505 nm to 560 nm, whereby a high intensity fluorescence image was obtained. An image of the fluorescence generated due to the laser light having the wavelength of 647 nm was taken via a filter member having a transmission wavelength band of 642 nm to 740 nm, whereby a low intensity fluorescence image was obtained. An image of the fluorescence generated due to the laser light having the wavelength of 405 nm was taken via a filter member having a transmission wavelength band of 430 nm to 505 nm, whereby a fluorescence image corresponding to the nucleus was obtained. In addition, a laser light whose wavelength was set between 430 nm to 480 nm was applied to the sample flowing in the flow cell. An image of light obtained as a result of this laser light having passed through the cell was taken via the filter member having a transmission wavelength band of 430 nm to 480 nm, whereby a bright field image was obtained. In the flow cytometer above, light having unnecessary wavelength bands is removed by a filter member or the like such that light having a target wavelength band is appropriately incident on the light receiver. It should be noted that, in this examination, the bright field image was obtained, but not limited thereto, a dark field image may be obtained.

Figure 4:
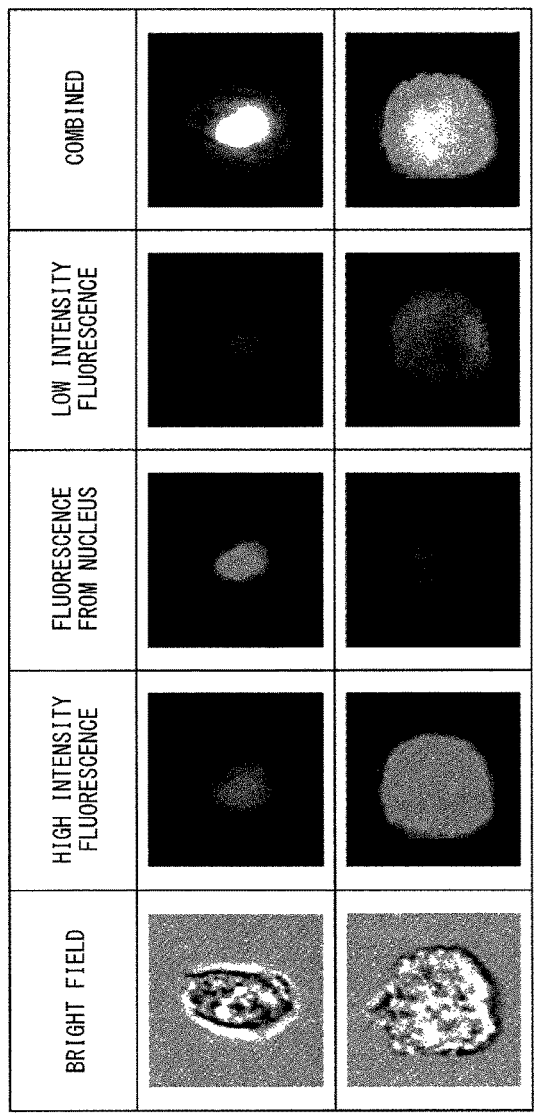
FIG. 4A shows images obtained in an examination according to Embodiment 1.
FIG. 4B shows numerical values obtained in the examination according to Embodiment 1.

With reference to FIG. 4A, images obtained through the detection above will be described.

"BRIGHT FIELD" indicates a bright field image of a cell. "HIGH INTENSITY FLUORESCENCE" and "LOW INTENSITY FLUORESCENCE" respectively correspond to an image based on high intensity fluorescence generated from the fluorescent dye labeling NF-κB, and an image based on low intensity fluorescence generated from the fluorescent dye labeling NF-κB. "FLUORESCENCE FROM NUCLEUS" corresponds to an image based on fluorescence generated from the nucleus staining dye that stains the nucleus. "COMBINED" corresponds to an image obtained by combining the four images on the left. The five images arranged along the horizontal direction are images obtained from one cell. Images in the columns of "HIGH INTENSITY FLUORESCENCE", "FLUORESCENCE FROM NUCLEUS", "LOW INTENSITY FLUORESCENCE", and "COMBINED" are gray scale expressions of the obtained color images, made for convenience. In the images in the columns of "HIGH INTENSITY FLUORESCENCE", "FLUORESCENCE FROM NUCLEUS", and "LOW INTENSITY FLUORESCENCE", each white portion indicates that the intensity of the fluorescence is high.

In the case of the cell shown in the upper row, in the image based on the low intensity fluorescence, the intensity is too low. Thus, localization of NF-κB is difficult to be identified. On the other hand, in the image based on the high intensity fluorescence, the intensity is appropriate. Thus, it is possible to identify that NF-κB is localized in the nucleus. In the case of the cell shown in the lower row, in the image based on the high intensity fluorescence, the intensity is too high. Thus, localization of NF-κB is difficult to be identified. On the other hand, in the image based on the low intensity fluorescence, the intensity is appropriate. Thus, it is possible to identify that NF-κB is localized in the cytoplasm.

5. Calculation of Nuclear Localization Percentage

Localization of NF-κB was identified for each cell by viewing the obtained images. This identification was performed in the same manner as described in step S4 above. That is, the nucleus region was set on the basis of the image of the fluorescence from the nucleus, and the region other than the nucleus region was set as the cytoplasm region. Then, when it was considered that the fluorescence intensity of the nucleus was higher than or equal to about twice of the fluorescence intensity of the cytoplasm, it was determined that NF-κB was localized in the nucleus in this cell. When it was considered that the fluorescence intensity of the nucleus was less than about twice of the fluorescence intensity of the cytoplasm, it was determined that NF-κB was localized in the cytoplasm in this cell.

With reference to FIG. 4B, regarding 131 cells recognized by the flow cytometer above, the result of the identification of localization of NF-κB will be described.

The number of cells for which localization in the nucleus could be identified was 44, and the number of cells for which localization in the cytoplasm could be identified was 87. The number of cells for which localization was not identified was 0. The nuclear localization percentage at this time was: 44/131=34%.

Described below are: Comparative Example 1 in which localization was identified only on the basis of high intensity fluorescence images; and Comparative Example 2 in which localization was identified only on the basis of low intensity fluorescence images. In the case of Comparative Example 1, the number of cells for which localization in the nucleus could be identified was 42, and the number of cells for which localization in the cytoplasm could be identified was 10. The number of cells for which localization could not be identified because of their too high fluorescence intensities was 79. The nuclear localization percentage in Comparative Example 1 was 81%. In the case of Comparative Example 2, the number of cells for which localization in the nucleus could be identified was 16, and the number of cells for which localization in the cytoplasm could be identified was 84. The number of cells for which localization could not be identified because of their too low fluorescence intensities was 31. The nuclear localization percentage in Comparative Example 2 was 16%.

As described above, this examination shows that, when localization is to be identified on the basis of two fluorescence images having different intensities as in Embodiment 1, even with respect to the cells for which identification could not be made in Comparative Examples 1 and 2, localization of NF-κB can be identified. In addition, when localization is identified as in Embodiment 1, the number of cells for which identification cannot be made is small. Thus, localization of NF-κB in the cell can be accurately identified. Therefore, according to Embodiment 1, while the number of cells for which identification cannot be made is kept at a low level, localization of NF-κB can be accurately identified. Thus, for example, even when the number of cells collected from a subject is small, it is possible to accurately identify localization of NF-κB, while ensuring the number of cells for which the identification can be made.

Embodiment 1 has shown an example in which the localization state of NF-κB is identified, as an identification of the distribution state of a test substance. However, when the amount of test substance molecules changes, the amount of the molecules may be judged. In such a case, the operator labels the molecules with the fluorescent substances 11 and 12, and the processing apparatus obtains images on the basis of two fluorescences having different intensities generated from the fluorescent substances 11 and 12. When the amount of the molecules is large, the operator judges the amount by using a low intensity fluorescence image, and when the amount of the molecules is small, the operator judges the amount by using a high intensity fluorescence image. Accordingly, the amount of the molecules can be accurately judged.

Apparatus Configuration in Embodiment 1

Description will be given of a configuration of a cell information obtaining apparatus which takes an image of each cell and which identifies localization of a test substance in the cell on the basis of the cell information obtaining method according to Embodiment 1.

Figure 5:
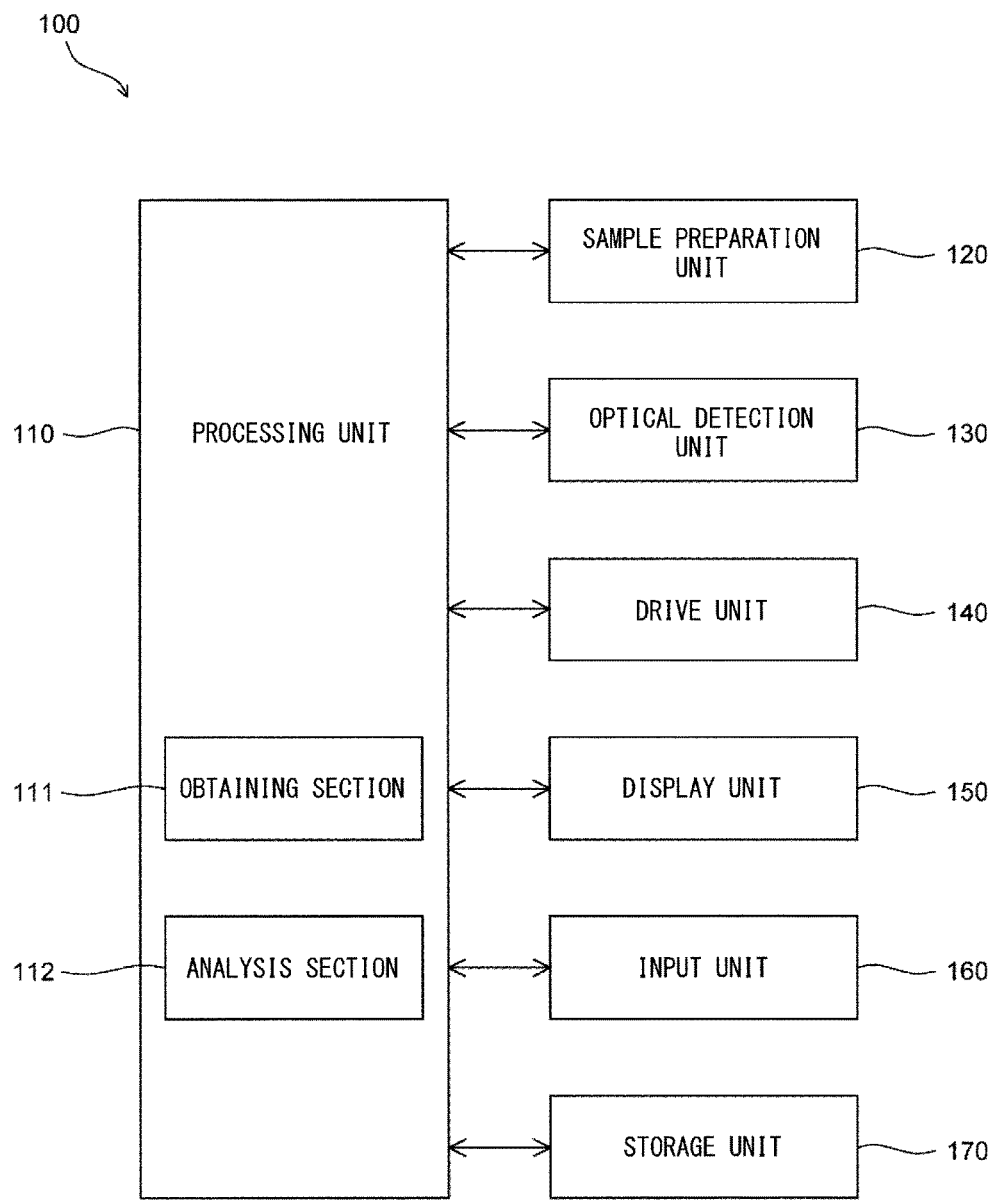
FIG. 5 is a block diagram showing a configuration of an apparatus according to Embodiment 1.

As shown in FIG. 5, a cell information obtaining apparatus 100 includes a processing unit 110, a sample preparation unit 120, an optical detection unit 130, a drive unit 140, a display unit 150, an input unit 160, and a storage unit 170.

The processing unit 110 is implemented by a microcomputer, a CPU, and the like. The storage unit 170 is implemented by a RAM, a ROM, a hard disk, and the like. In the storage unit 170, process programs to be executed by the processing unit 110 and various data such as images are stored. The processing unit 110 transmits/receives signals to/from components of the cell information obtaining apparatus 100, and controls the components. The processing unit 110 is provided with functions as an obtaining section 111 and an analysis section 112 by a program stored in the storage unit 170.

The sample preparation unit 120 prepares a sample by mixing cells and reagents in accordance with step S1 shown in FIG. 1. The sample preparation may be performed by the operator. In such a case, the sample preparation unit 120 is omitted from the cell information obtaining apparatus 100. The optical detection unit 130 is a flow cytometer. The optical detection unit 130 applies light to each cell contained in a sample and takes an image of generated fluorescence. The configuration of the optical detection unit 130 will be described later with reference to FIG. 6. The drive unit 140 drives light sources 301 to 304 of the optical detection unit 130 described later.

The display unit 150 is implemented by a display. The display unit 150 displays images obtained for each cell, localization of NF-κB identified for each cell, the number of cells in each of which NF-κB is localized in the nucleus, the number of cells in each of which NF-κB is localized in the cytoplasm, a nuclear localization percentage, a cytoplasmic localization percentage, and the like. The input unit 160 is implemented by a mouse and a keyboard. The operator inputs instructions to the cell information obtaining apparatus 100 via the input unit 160.

Figure 6:
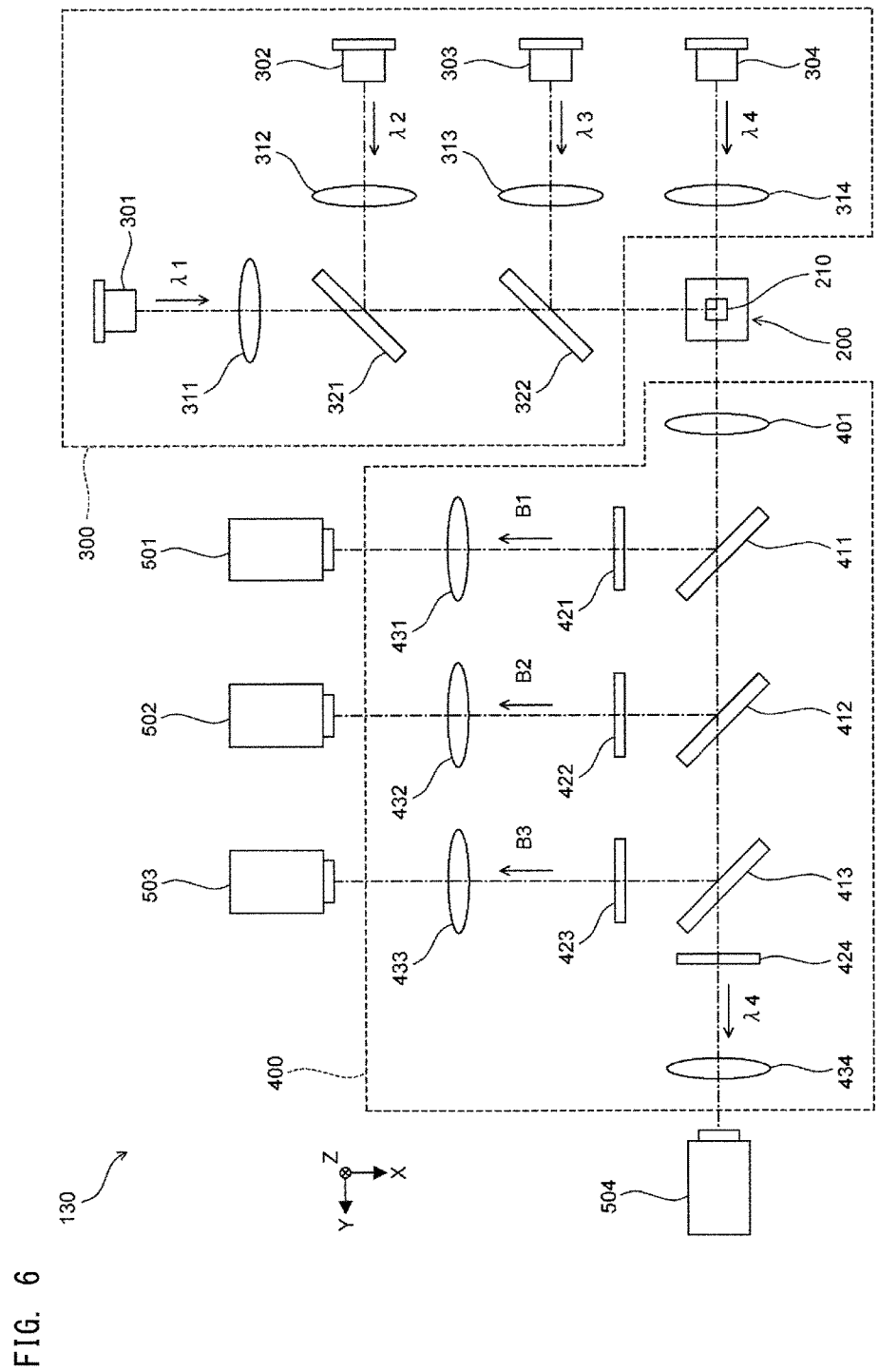
FIG. 6 shows a configuration of an optical detection unit according to Embodiment 1.

As shown in FIG. 6, the optical detection unit 130 includes a flow cell 200, a light application unit 300, a light condensing unit 400, and light receivers 501 to 504. The flow cell 200 has a flow pass 210 formed therein. In the flow pass 210, the sample prepared by the sample preparation unit 120 is caused to flow. In FIG. 6, XYZ axes orthogonal to one another are shown for convenience.

The light application unit 300 applies light to each cell contained in the sample flowing in the flow cell 200, thereby to cause fluorescence having different intensities to be generated from the fluorescent substances 11 and 12 shown in FIG. 2. In addition, the light application unit 300 applies light to the cell, thereby to cause fluorescence to be generated from the fluorescent substance 13 shown in FIG. 2. Further, the light application unit 300 applies light for bright field to the cell. The light application unit 300 includes the light sources 301 to 304, condenser lenses 311 to 314, and dichroic mirrors 321 and 322.

The light sources 301 to 304 are each implemented by a semiconductor laser light source. Lights emitted from the light sources 301 to 304 are laser lights having the wavelengths $\lambda 1$ to $\lambda 4$, respectively. The wavelengths $\lambda 1$ to $\lambda 4$ respectively are 488 nm, 647 nm, 405 nm, and 785 nm, for example. The laser lights having the wavelengths $\lambda 1$ to $\lambda 3$ are lights for exciting fluorescences from the fluorescent substances 11 to 13, respectively, as shown in FIG. 2. The condenser lens 311 to 314 condense lights emitted from the light sources 301 to 304, respectively. The dichroic mirror 321 allows light having the wavelength $\lambda 1$ to pass therethrough, and reflects light having the wavelength $\lambda 2$. The dichroic mirror 322 allows lights having the wavelengths $\lambda 1$ and $\lambda 2$ to pass therethrough, and reflects light having the wavelength $\lambda 3$.

Thus, the light application unit 300 applies, in a superposed manner, the lights having the wavelengths $\lambda 1$ to $\lambda 3$ emitted from the light sources 301 to 303, to each cell contained in the sample flowing in the flow pass 210. In addition, the light application unit 300 applies light having the wavelength $\lambda 4$ to the position, in the flow pass 210, at which the lights having the wavelengths $\lambda 1$ to $\lambda 3$ are applied. When the lights having the wavelengths $\lambda 1$ to $\lambda 3$ are applied to the sample flowing in the flow cell 200, fluorescences having different wavelength bands are generated from the fluorescent substances 11 to 13, respectively, as described with reference to FIG. 2. When light having the wavelength $\lambda 4$ is applied to the sample flowing in the flow cell 200, this light passes through the cell. The light having the wavelength $\lambda 4$ that has passed through the cell is used for obtaining a bright field image.

Here, the light source 301 emits light having the wavelength $\lambda 1$ at a high power, and the light source 302 emits light having the wavelength $\lambda 2$ at a low power. The emission power of each of the light sources 301 and 302 is controlled by the drive unit 140 shown in FIG. 5. Accordingly, as described with reference to FIG. 2, the fluorescence generated from the fluorescent substance 11 has a high intensity, and the fluorescence generated from the fluorescent substance 12 has a low intensity. It should be noted that in Embodiment 1 and Embodiments 2 and 3 described later, the emission power of each of the light sources 301 and 302 may not be adjusted. If a fluorescence label is selected that has the same emission power but that causes a difference in obtained fluorescence intensities, fluorescence generated from the fluorescent substance 11 will have a high intensity, and fluorescence generated from the fluorescent substance 12 will have a low intensity.

The light condensing unit 400 is for condensing fluorescences generated at the flow cell 200 as a result of application of lights having the wavelengths $\lambda 1$ to $\lambda 3$. The light condensing unit 400 causes fluorescences generated from the fluorescent substances 11 to 13, to be condensed onto the light receivers 501 to 503, respectively. The light condensing unit 400 causes light having the wavelength $\lambda 4$ generated at the flow cell 200, to be condensed onto the light receiver 504. The light condensing unit 400 includes a condenser lens 401, filter members 411 to 413 and 421 to 424, and condenser lenses 431 to 434.

The condenser lens 401 condenses fluorescence generated from the sample flowing in the flow cell 200, and light having the wavelength $\lambda 4$ that has passed through the sample flowing in the flow cell 200. The filter members 411 to 413 are each implemented by a dichroic mirror.

Among the lights condensed by the condenser lens 401, the filter member 411 reflects the light having the wavelength band B1 and allows light other than the light having the wavelength band B1 to pass therethrough. Of the light reflected by the filter member 411, the filter member 421 allows only the light having the wavelength band B1 to pass therethrough, and blocks light other than the light having the wavelength band B1. In this manner, the filter members 411 and 421 are each configured to be able to separate only the fluorescence having the wavelength band B1, among the lights generated at the flow cell 200. Similarly, the filter members 412 and 422 are each configured to be able to separate only the fluorescence having the wavelength band B2, among the lights generated at the flow cell 200. The filter members 413 and 423 are each configured to be able to separate only the fluorescence having the wavelength band B3, among the lights generated at the flow cell 200. Among the lights that have passed through the filter members 411 to 413, the filter member 424 allows the light having the wavelength $\lambda 4$ to pass therethrough and blocks light other than the light having the wavelength $\lambda 4$.

The light receiver 501 receives the light having the wavelength band B1 and having been condensed by the condenser lens 431, and outputs, as an image pickup signal, image information based on the received light. The light receiver 502 receives the light having the wavelength band B2 and having been condensed by the condenser lens 432, and outputs, as an image pickup signal, image information based on the received light. The light receiver 503 receives the light having the wavelength band B3 and having been condensed by the condenser lens 433, and outputs, as an image pickup signal, image information based on the received light. The light receiver 504 receives the light having the wavelength $\lambda 4$ and having been condensed by the condenser lens 434, and outputs, as an image pickup signal, image information based on the received light. The light receivers 501 to 504 are each implemented by an image pickup device such as a color CCD, for example.

The light condensing unit 400 causes the lights having the wavelength bands B1 to B3 and the light having the wavelength $\lambda 4$ to be condensed onto the light receivers 501 to 504, respectively. However, the light condensing unit 400 may cause those lights to form images on a single light receiver. In such a case, the optical detection unit 130 is configured such that the lights having the wavelength bands B1 to B3 and the light having the wavelength $\lambda 4$ form images in different regions, respectively, on the light receiving surface of the light receiver.

Figure 7:
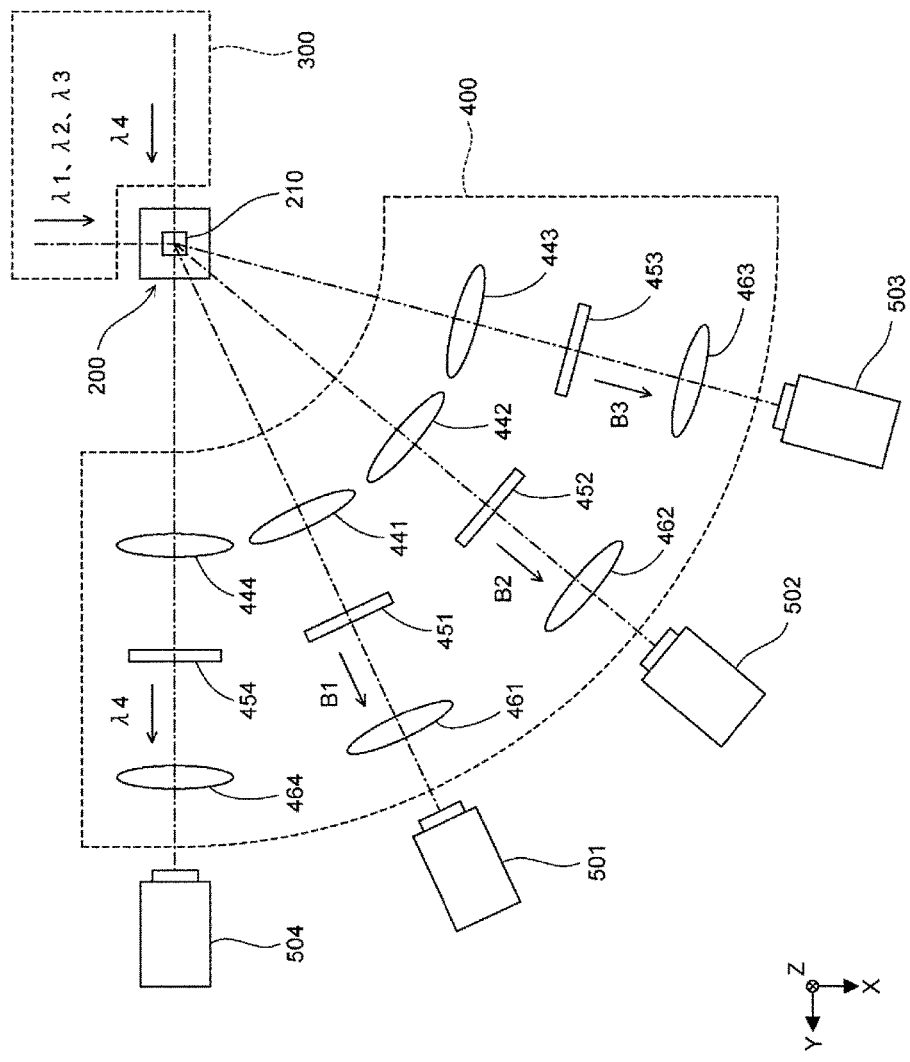
FIG. 7 shows a configuration of an optical detection unit according to a modification of Embodiment 1.

In the configuration shown in FIG. 6, a plurality of filter members are used in order to separate the lights having the wavelength bands B1 to B3. However, as shown in FIG. 7, the lights generated at the flow cell 200 may be separated by a single filter member. As shown in FIG. 7, the light condensing unit 400 includes condenser lenses 441 to 444, filter members 451 to 454, and condenser lenses 461 to 464. Lights having the wavelength bands B1 to B3 are separated by the filter members 451 to 453, respectively, and light having the wavelength $\lambda 4$ is separated by the filter member 454.

Next, with reference to the flow chart shown in FIG. 8, a case where the process of step S4 shown in FIG. 1 is performed by the cell information obtaining apparatus 100 will be described.

Figure 8:
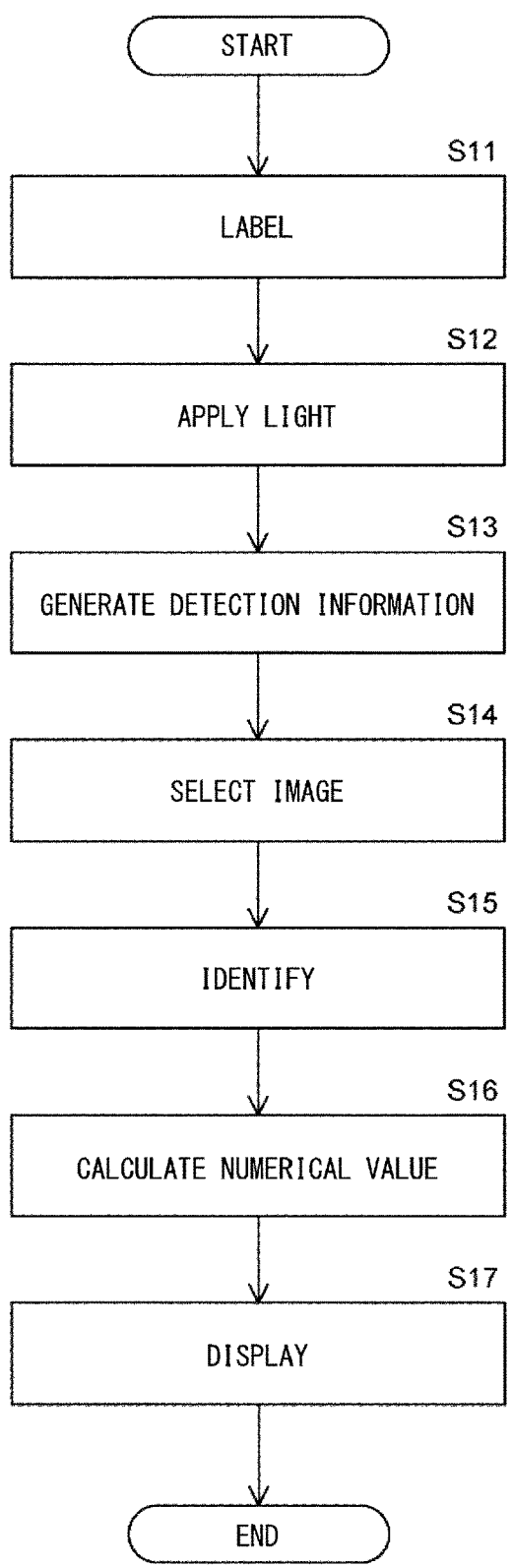
FIG. 8 is a flow chart showing a process performed by a cell information obtaining apparatus according to Embodiment 1.

As shown in FIG. 8, in step S11, the processing unit 110 drives the sample preparation unit 120. As in step S1 shown in FIG. 1, the processing unit 110 causes the sample preparation unit 120 to label NF-κB contained in each cell with the fluorescent substances 11 and 12, and to label the nucleus contained in the cell with the fluorescent substance 13, thereby preparing a sample. In step S12, the processing unit 110 causes the sample to flow in the flow cell 200. The processing unit 110 causes the drive unit 140 to drive the light sources 301 to 304, and then, causes light to be applied to the cell flowing in the flow cell 200. In step S13, the processing unit 110 causes the light receivers 501 to 503 to take images of fluorescences having the wavelength bands B1 to B3, respectively. The processing unit 110 causes the light receiver 504 to take an image of light having the wavelength $\lambda 4$. Then, the obtaining section 111 of the processing unit 110 obtains images on the basis of image pickup signals outputted by the light receivers 501 to 504.

In step S14, the analysis section 112 of the processing unit 110 selects an image that allows identification of localization, from a high intensity fluorescence image and a low intensity fluorescence image. Specifically, from the high intensity fluorescence image and the low intensity fluorescence image, the analysis section 112 selects an image in which the intensity (e.g., the brightness of the entire image) of the fluorescence obtained from the image is within a predetermined range. Accordingly, an image having an extremely high fluorescence intensity and an image having an extremely low fluorescence intensity are excluded from images to be used in identification of localization of NF-κB, because such images do not enable the identification as in the case of the image 32 and the image 41 in FIG. 3.

In addition, from the high intensity fluorescence image and the low intensity fluorescence image, the analysis section 112 selects an image in which the difference between the fluorescence intensity at an analysis target site of the cell and the fluorescence intensity in the portion other than the analysis target site in the cell is greater than a predetermined threshold. In Embodiment 1, the analysis target site is nucleus. That is, an image is selected in which the difference between the fluorescence intensity inside the nucleus and the fluorescence intensity in the portion outside the nucleus in the cell is greater than a predetermined threshold. As a result, an image having a small difference between the fluorescence intensity inside the nucleus and the fluorescence intensity outside the nucleus is excluded from images to be used in identification of localization of NF-κB, because such an image does not enable the identification as in the case of the image 32 and the image 41 in FIG. 3.

Next, in step S15, the analysis section 112 identifies localization of NF-κB in each cell, by using the image selected in step S14. That is, the analysis section 112 calculates the proportion of the localization amount of NF-κB at the analysis target site in the cell relative to the localization amount of NF-κB in the entirety of the cell. For example, with respect to the image selected in step S14, the analysis section 112 divides the fluorescence intensity in the nucleus region by the fluorescence intensity in the entire region of the cell. When the division result is 2 or greater, the analysis section 112 identifies that NF-κB is localized in the nucleus. When the division result is smaller than 2, the analysis section 112 identifies that NF-κB is localized in the cytoplasm. The criterion value used for determining the division result is not limited to 2, and may be another value.

In a case where two images are selected in step S14, then, in step S15, with respect to each of both images, the division result is obtained and localization is identified, as described above. In a case where no image is selected in step S14, then, in step S15, localization of this cell is categorized as "cannot be identified".

In step S16, on the basis of the identification results of all the cells that have been subjected to the process, the analysis section 112 calculates the nuclear localization number, the cytoplasmic localization number, the nuclear localization percentage, and the cytoplasmic localization percentage described above. In step S17, the processing unit 110 causes the display unit 150 to display the numerical values calculated in step S16, the images obtained for each cell, the identification result for each cell, and the like. Specifically, the processing unit 110 causes the display unit 150 to display a screen 161 including the above contents.

Figure 9:
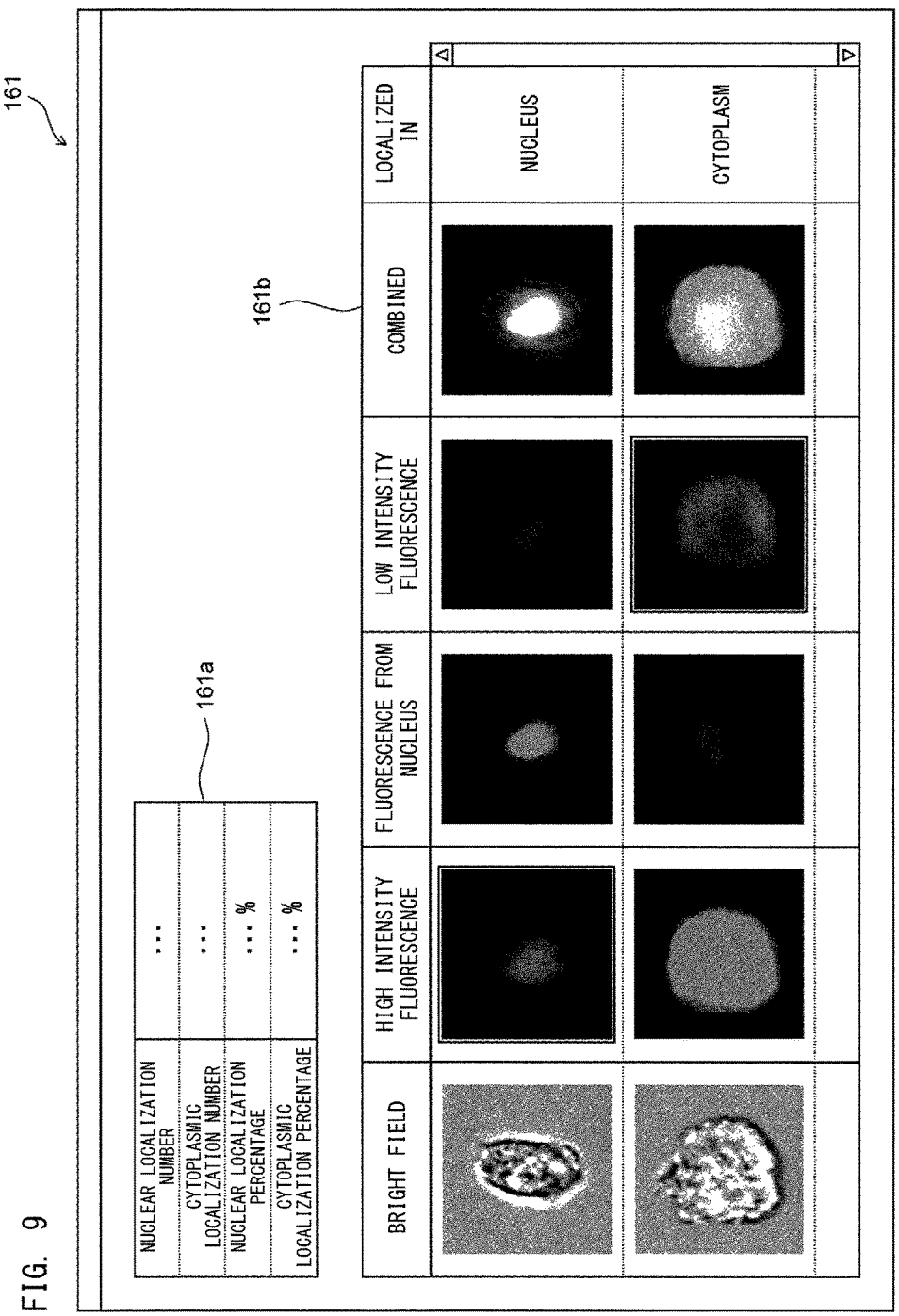
FIG. 9 shows a screen to be displayed on a display unit according to Embodiment 1.

As shown in FIG. 9, the screen 161 includes regions 161a and 161b. The region 161a shows the nuclear localization number, the cytoplasmic localization number, the nuclear localization percentage, and the cytoplasmic localization percentage. The region 161b shows the images and the results of identification of NF-κB localization. In the region 161b, the image used in the identification of localization in step S15 is surrounded by a solid line so as to indicate that the image was used in the localization identification.

The fluorescence information obtained in step S13 may be a waveform signal that indicates fluorescence intensity changing with time. In such a case, in the optical detection unit 130, photodetectors such as photomultipliers are disposed as the light receivers 501 to 503. Three photodetectors receive the high intensity fluorescence having the wavelength band B1, the low intensity fluorescence having the wavelength band B2, and the fluorescence having the wavelength band B3, and outputs waveform signals indicating the fluorescence intensities, respectively.

Figure 10:
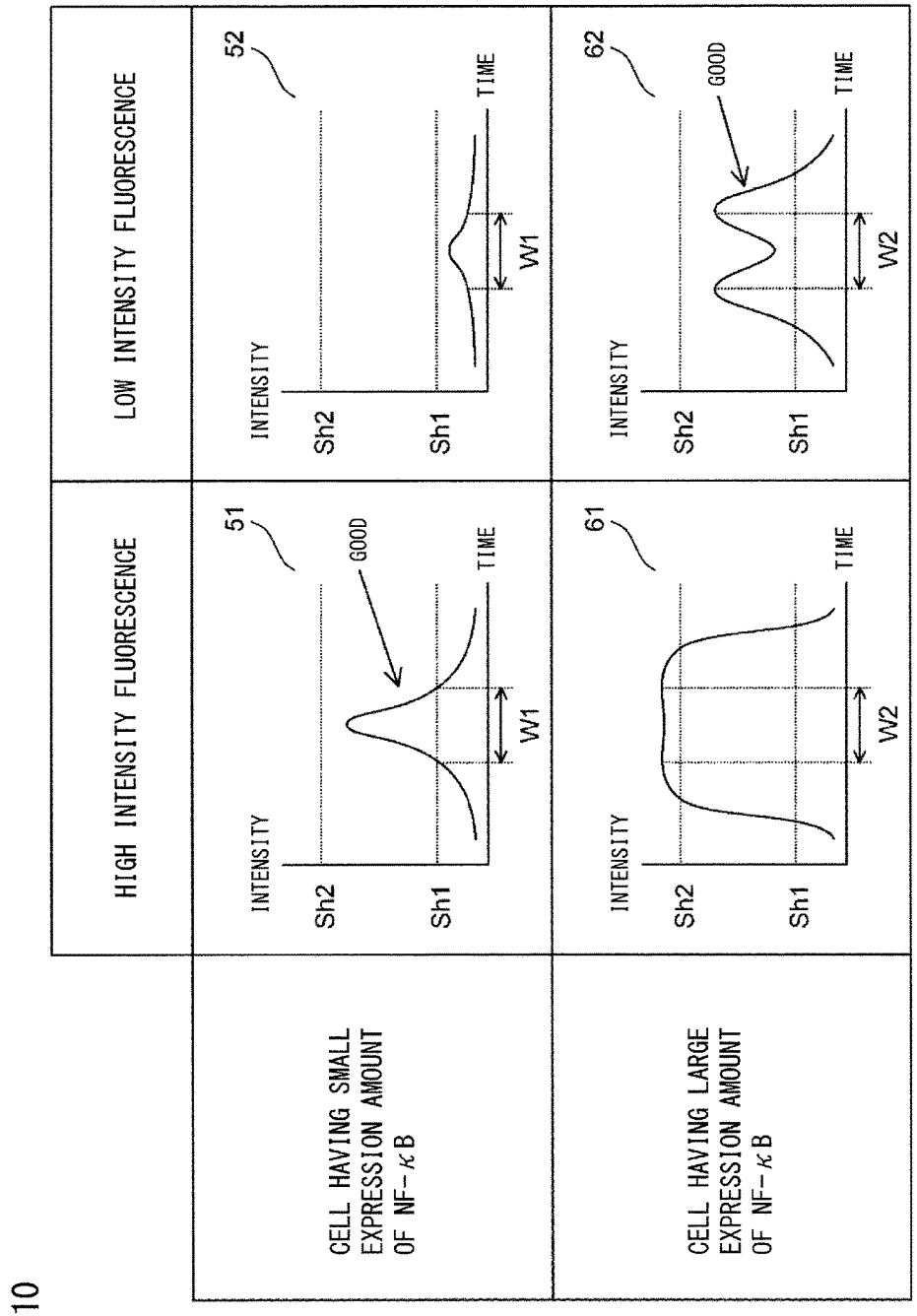
FIG. 10 is a conceptual diagram showing graphs obtained on the basis of high intensity fluorescence and low intensity fluorescence according to a modification of Embodiment 1.

As shown in FIG. 10, on the basis of the waveform signals outputted by the photodetectors, the analysis section 112 obtains, for example, graphs 51 and 52 in the case of a cell having a small expression amount of NF-κB, and obtains, for example, graphs 61 and 62 in the case of a cell having a large expression amount of NF-κB. On the basis of a waveform signal outputted by a photodetector, the analysis section 112 obtains a graph that corresponds to the nucleus. On the basis of the graph regarding the nucleus obtained simultaneously with the graphs 51 and 52, the analysis section 112 sets a width W1 of a waveform that corresponds to the nucleus in the graphs 51 and 52. On the basis of the graph regarding the nucleus obtained simultaneously with the graphs 61 and 62, the analysis section 112 sets a width W2 of a waveform that corresponds to the nucleus in the graphs 61 and 62.

According to the graph 51, the peak value of the fluorescence is between thresholds Sh1 and Sh2, and the peak of the waveform is present within the width W1 that corresponds to the nucleus. Thus, the analysis section 112 can identify that NF-κB is localized in the nucleus. On the other hand, according to the graph 52, the peak value of the fluorescence is smaller than the threshold Sh1. Thus, the analysis section 112 cannot identify localization of NF-κB. According to the graph 61, the peak value of the fluorescence is greater than the threshold Sh2. Thus, the analysis section 112 cannot identify localization of NF-κB. On the other hand, according to the graph 62, the peak value of the fluorescence is between the thresholds Sh1 and Sh2, and a depression in the waveform is present within the width W2 that corresponds to the nucleus. Thus, the analysis section 112 can identify that NF-κB is localized in the cytoplasm. Therefore, also in this case, as in the case where images are used as shown in FIG. 3, localization of NF-κB can be accurately identified on the basis of two fluorescences having different intensities.

Embodiment 2

In Embodiment 2, not by using two lights, but by using only the light having the wavelength λ1, fluorescences having different intensities from each other are obtained. In Embodiment 2, among the steps of the cell information obtaining method shown in FIG. 1, only some procedures in steps S1 and S2 are different from those in Embodiment 1. In the following, the procedures that are different from those in Embodiment 1 will be described.

Figure 11:
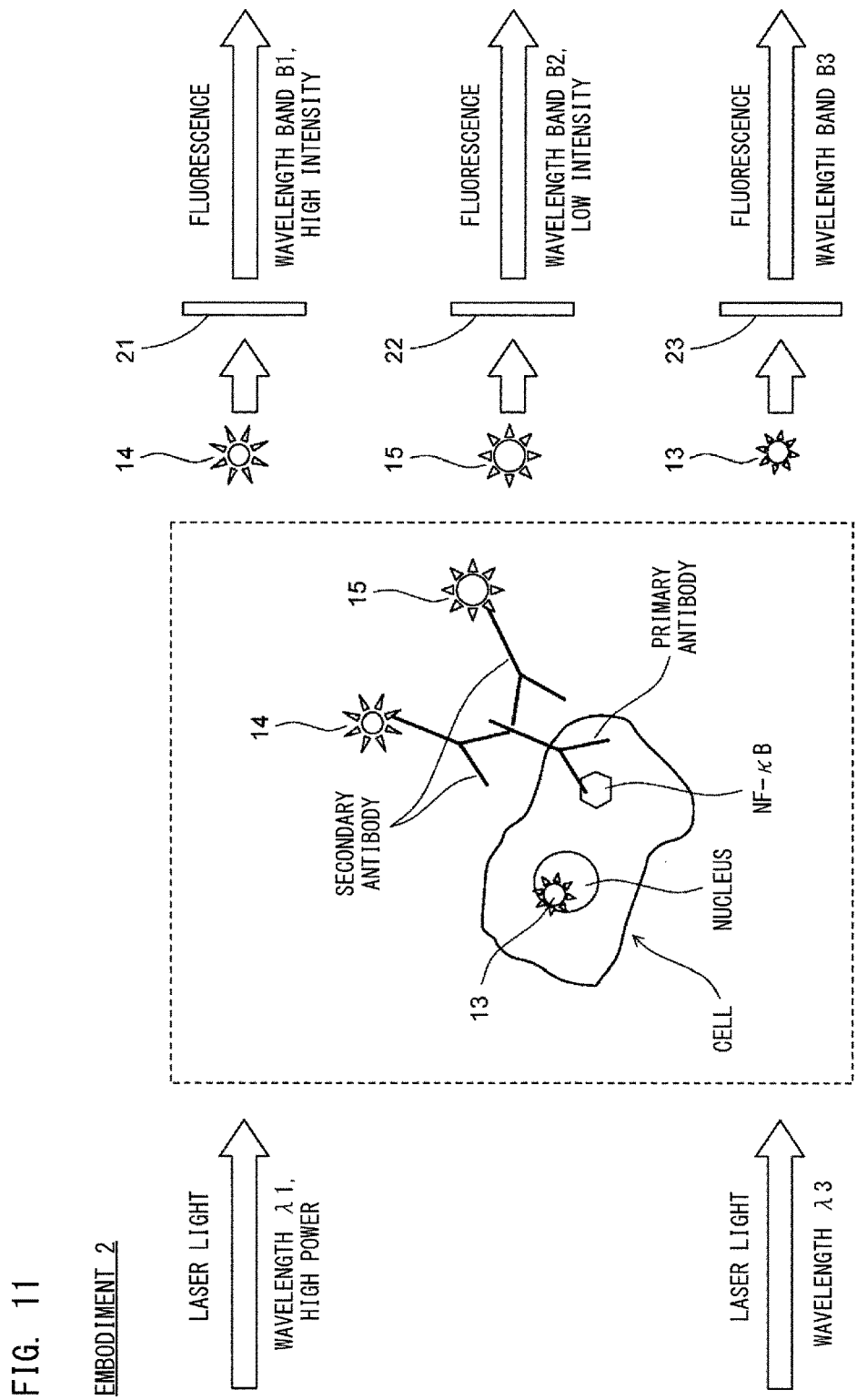
FIG. 11 shows the outline of how to obtain fluorescence according to Embodiment 2.

In step S1, as shown in FIG. 11, NF-κB contained in each cell is labeled with fluorescent substances 14 and 15 having different fluorescence wavelengths from each other. The fluorescent substances 14 and 15 are each a fluorescent dye. When irradiated with light having the wavelength λ1, the fluorescent substance 14 excites fluorescence having the same wavelength band as that of the fluorescent substance 11 in Embodiment 1. When irradiated with light having the wavelength λ1, the fluorescent substance 15 excites fluorescence having the same wavelength band as that of the fluorescent substance 12 shown in FIG. 2. That is, for the fluorescent substances 14 and 15, the wavelength of the excitation light is substantially the same.

In step S2, a sample containing the cells labeled with the fluorescent substances 14, 15, and 13 is caused to flow in the flow cell. Lights respectively having the wavelengths λ1 and λ3 are applied to each cell flowing in the flow cell, whereby fluorescences are generated from the fluorescent substances 14, 15, and 13, respectively. The fluorescences generated from the fluorescent substances 14 and 15 are passed through the filter members 21 and 22, respectively, thereby becoming fluorescences having the wavelength bands B1 and B2, respectively. Here, the fluorescent substances 14 and 15 are configured such that the fluorescence having the wavelength band B1 has a high intensity and the fluorescence having the wavelength band B2 has a low intensity.

Compared with Embodiment 1, according to the apparatus configuration in Embodiment 2, the light source 302, the condenser lens 312, and the dichroic mirror 321 are omitted in the optical detection unit 130 shown in FIG. 6.

Also in Embodiment 2, as in Embodiment 1, high intensity fluorescence having the wavelength band B1 and low intensity fluorescence having the wavelength band B2 are generated, whereby a high intensity fluorescence image and a low intensity fluorescence image can be obtained. Accordingly, as in Embodiment 1, on the basis of the high intensity fluorescence image and the low intensity fluorescence image, NF-κB having diverse distribution and amount in the cell can be accurately analyzed.

Embodiment 3

In Embodiment 3, not by using two lights and two fluorescent substances, but by using a single light having the wavelength λ1 and a single fluorescent substance 11, fluorescences having different intensities from each other are obtained. In Embodiment 3, among the steps of the cell information obtaining method shown in FIG. 1, only some procedures in steps S1 and S2 are different from those in Embodiment 1. In the following, the procedures that are different from those in Embodiment 1 will be described.

Figure 12:
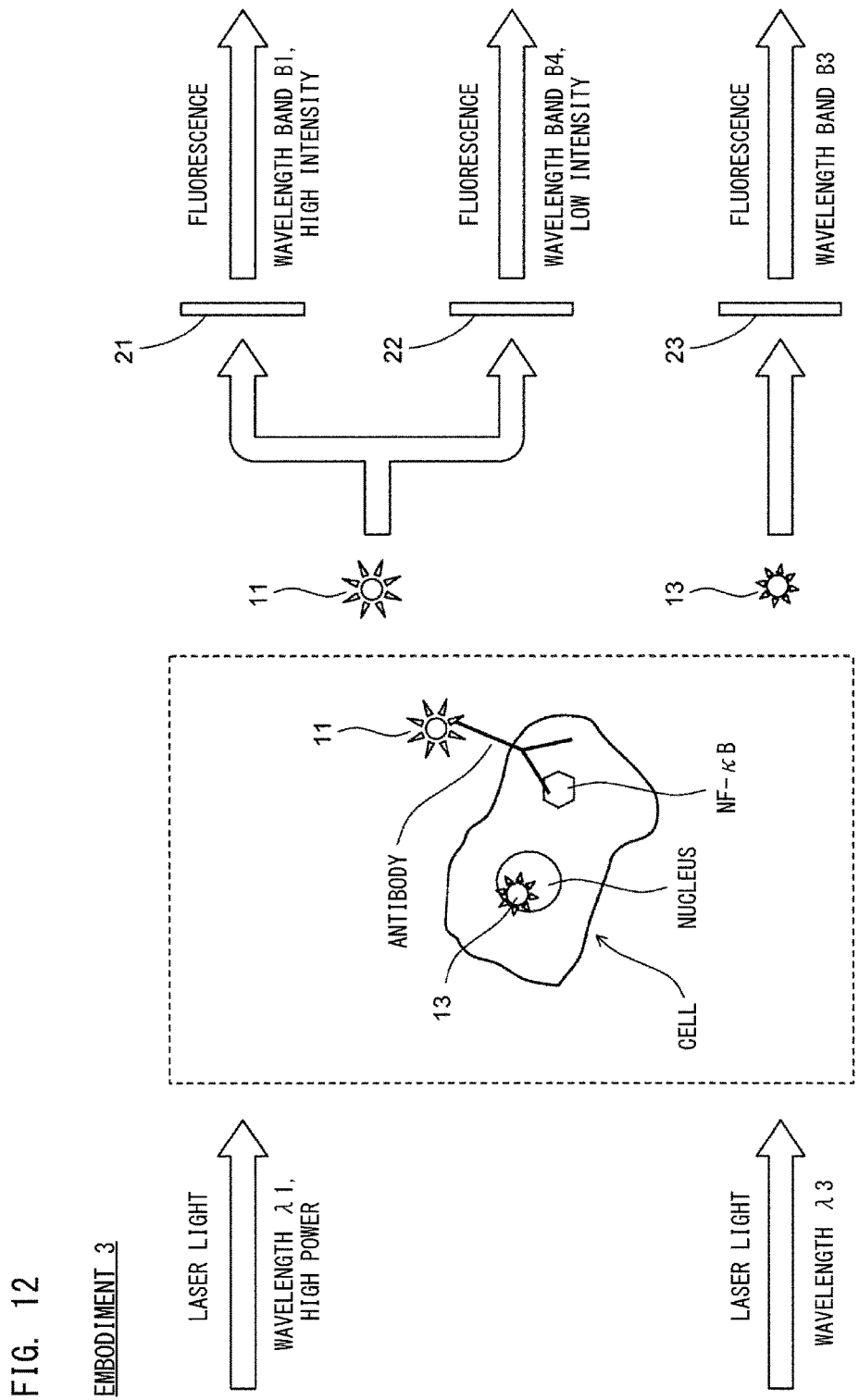
FIG. 12 shows the outline of how to obtain fluorescence according to Embodiment 3.

In step S1, as shown in FIG. 12, NF-κB contained in each cell is labeled with only the fluorescent substance 11 as used in Embodiment 1. At this time, the fluorescent substance 11 may be bound to NF-κB via a single antibody. In step S2, a sample containing the cells labeled with the fluorescent substances 11 and 13 is caused to flow in the flow cell. Lights respectively having the wavelengths λ1 and 23 are applied to each cell flowing in the flow cell, whereby fluorescences are generated from the fluorescent substance 11 and 13, respectively.

Figure 13:
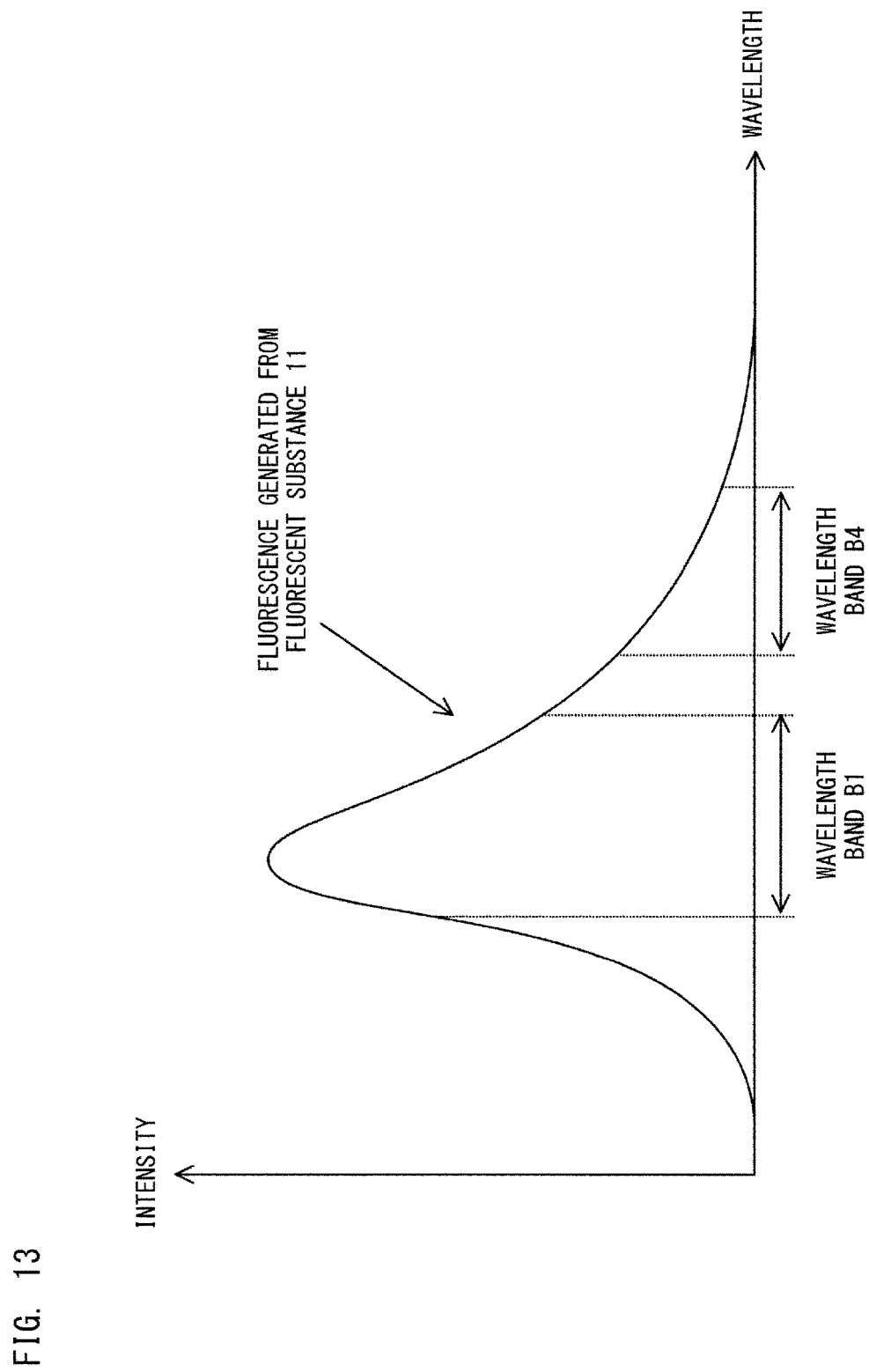
FIG. 13 is a diagram for explaining the transmission wavelength band of a filter member and wavelength bands of fluorescence to be obtained according to Embodiment 3.

As shown in FIG. 12, the fluorescence generated from the fluorescent substance 11 is divided into two, one of which is caused to pass through the filter member 21 as used in Embodiment 1, and the other of which is caused to pass through the filter member 22 as used in Embodiment 1. The filter member 21 allows only light having the wavelength band B1 to pass therethrough. The filter member 22 allows only light having a wavelength band B4 to pass therethrough. As shown in FIG. 13, the wavelength band B1 includes, for example, a wavelength at which the intensity of the fluorescence generated from the fluorescent substance 11 peaks. The wavelength band B4 is set to, for example, a wavelength band that contains longer wavelengths than those of the wavelength band B1, and that does not overlap the wavelength band B1. As a result, as shown in FIG. 12, the fluorescence having the wavelength band B1 and having passed through the filter member 21 has a high intensity, and the fluorescence having the wavelength band B4 and having passed through the filter member 22 has a low intensity.

It should be noted that the wavelength band B1 may not necessarily contain a wavelength at which the intensity of the fluorescence generated from the fluorescent substance 11 peaks. The wavelength band B4 may be set to a wavelength band that contains shorter wavelengths than those of the wavelength band B1. The wavelength band B4 may partially overlap the wavelength band B1.

Examination of Embodiment 3

Next, examination of Embodiment 3 performed by the inventor will be described.

1. Preparation

As the cells, human cardiac microvascular endothelial cell (HMVEC-C) (Lonza Cat No. CC-7030, Lot No. 0000296500 (P4)) were obtained. As the primary antibody, NF-κB p65 (D14E12) XP Rabbit mAb (Cell Signaling Technologies #8242S) was obtained. As the secondary antibody, Goat anti-Rabbit IgG (H+L) Secondary Antibody, Alexa Fluor 647 conjugate (Life technologies A-21245) was obtained. To the secondary antibody, Alexa Fluor 647 was bound, as the fluorescent dye. Other than these, EGM-2MV Medium (Lonza Cat No. CC-3202), EGM-2MV SingleQuots Kit (Lonza Cat No. CC-3202), PBS pH7.4 (GIBCO Cat No. 10010-023), BSA (LAMPIRE Cat No. 7500805), PFA (WAKO Cat No. 160-16061), and TritonX100 (Nacalai Tesque Cat No. 35501-15) were obtained.

2. Reagent Preparation

EGM-2MV SingleQuots Kit was added to 500 mL of EGM-2MV Medium, to create a culture medium. Paraformaldehyde was dissolved in pH12 PBS so as to have a final concentration of 8% w/v, and then, the pH was adjusted to 7.4. 1.5 g of BSA was added to and dissolved in PBS, and PBS was additionally added thereto to obtain 50 mL, whereby 3% BSA/PBS was prepared. 0.5 g of BSA was added to and dissolved in PBS, and PBS was additionally added thereto to obtain 50 mL, whereby 1% BSA/PBS was prepared. TritonX100 was adjusted with PBS so as to have a final concentration of 0.1% w/v.

3. Procedure

HMVEC-C cells were cultured in the EGM-2MV culture medium in accordance with a manufacturer-recommended protocol. Cells within six passages after the purchase thereof were used in this examination. The shelf life of the culture medium after opening was set to three weeks. For TNF-α-stimulated culture, the culture supernatant of about 70% confluent HMVEC-C cells was removed, and an EGM-2MV culture medium to which Recombinant Human TNF-alpha had been added so as to have a final concentration of 25 ng/mL was added. Then, the resultant mixture was left still for 1 hour in a 37° C. $CO^2$ incubator. The culture medium was removed with an electric pipette, with about 3 mL left, and the cells were detached with a scraper. 8% PFA/PBS was added by an amount equivalent to the collected suspension, and the resultant mixture was allowed to react at room temperature for 15 minutes. At room temperature, centrifugal separation was performed at 1000 rpm for 3 minutes. The cell pellet was washed with 1 mL of PBS twice. The supernatant was removed, and 1 mL of 0.1% Triton X-100/PBS was added. Then, the resultant mixture was allowed to react at room temperature for 15 minutes. At room temperature, centrifugal separation was performed at 1000 rpm for 3 minutes. The cells were washed with 1 mL of 1% BSA/PBS twice. The supernatant was removed, and 1 mL of 3% BSA/PBS was added. Then, the resultant mixture was left still for 30 minutes at room temperature. 400 μL of the primary antibody diluted at a ratio of 1/1600 in 3% BSA/PBS was added. The resultant mixture was allowed to react at room temperature for 1 hour. At room temperature, centrifugal separation was performed at 1000 rpm for 3 minutes. The cells were washed with 1 mL of 1% BSA/PBS. 400 μL of the secondary antibody diluted at a ratio of 1/1000 in 3% BSA/PBS was added. The resultant mixture was allowed to react at room temperature for 30 minutes. The cells were washed with 1 mL of 1% BSA/PBS twice. The supernatant was removed and 50 μL of 1% BSA/PBS was added.

4. Detection by Flow Cytometer

As a flow cytometer that can obtain fluorescence images, ImageStreamX Mark II Imaging Flow Cytometer (Merck Millipore) was used. A sample prepared in accordance with the procedure 3 above was caused to flow in the flow cell of the flow cytometer. A laser light having a wavelength of 647 nm was applied to the sample flowing in the flow cell. The laser light having the wavelength of 647 nm corresponds to the laser light having the wavelength λ1 shown in FIG. 12. The emission power of the laser light having the wavelength of 647 nm was set to 10 mW. As a result of the application of the laser light having the wavelength of 647 nm to the fluorescent dye labeling NF-κB, fluorescence was generated.

In the flow cytometer above, an image of the fluorescence generated due to the laser light having the wavelength of 647 nm was taken via a filter member having a transmission wavelength band of 642 nm to 740 nm, whereby a high intensity fluorescence image was obtained. An image of the fluorescence generated due to the laser light having the wavelength of 647 nm was taken via a filter member having a transmission wavelength band of 740 nm to 800 nm, whereby a low intensity fluorescence image was obtained. In the flow cytometer above, light having unnecessary wavelength bands is removed by a filter member or the like such that light having a target wavelength band is appropriately incident on the light receiver.

Figure 14A:
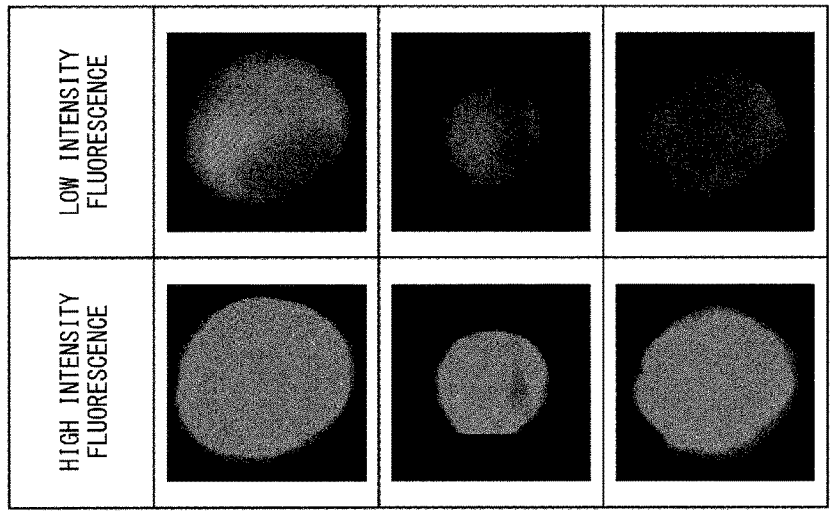
FIGS. 14A and 14B show images obtained in an examination according to Embodiment 3.
Figure 14B:
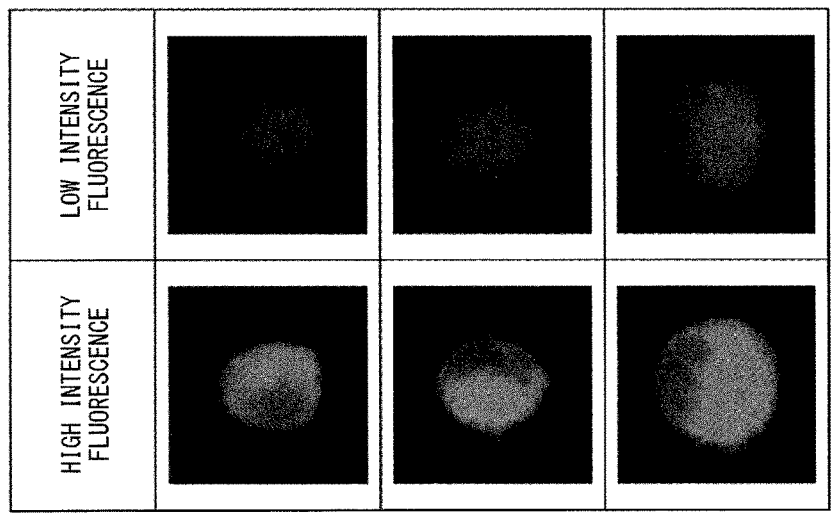

With reference to FIGS. 14A and 14B, images obtained through the detection above will be described.

"HIGH INTENSITY FLUORESCENCE" and "LOW INTENSITY FLUORESCENCE" are an image based on high intensity fluorescence generated from the fluorescent dye labeling NF-κB, and an image based on low intensity fluorescence generated from the fluorescent dye labeling NF-κB, respectively. In FIGS. 14A and 14B, the two images arranged along the horizontal direction are images obtained from one cell. The respective images are gray scale expressions of the obtained color images, made for convenience. In each image, the white portion indicates that the intensity of the fluorescence is high.

In the case of the three cells shown in FIG. 14A, in the image based on the low intensity fluorescence, the intensity is too low. Thus, localization of NF-κB is difficult to be identified. On the other hand, in the image based on the high intensity fluorescence, the intensity is appropriate. Thus, it is possible to identify that NF-κB is localized in the cytoplasm. In the case of the three cells shown in FIG. 14B, in the image based on the high intensity fluorescence, the intensity is too high. Thus, localization of NF-κB is difficult to be identified. On the other hand, in the image based on the low intensity fluorescence, the intensity is appropriate. Thus, it is possible to identify that NF-κB is localized in the cytoplasm.

As described above, this examination shows that, when localization is to be identified on the basis of two fluorescence images having different intensities as in Embodiment 3, localization of NF-κB can be identified. Thus, according to Embodiment 3, if fluorescence generated from one kind of fluorescent dye is allowed to pass through the filter members 21 and 22 which respectively allow fluorescences having different wavelength bands to pass therethrough, and two fluorescence images are obtained accordingly, it is possible to accurately identify localization of NF-κB through a single measurement for one cell.

Apparatus Configuration in Embodiment 3

Figure 15:
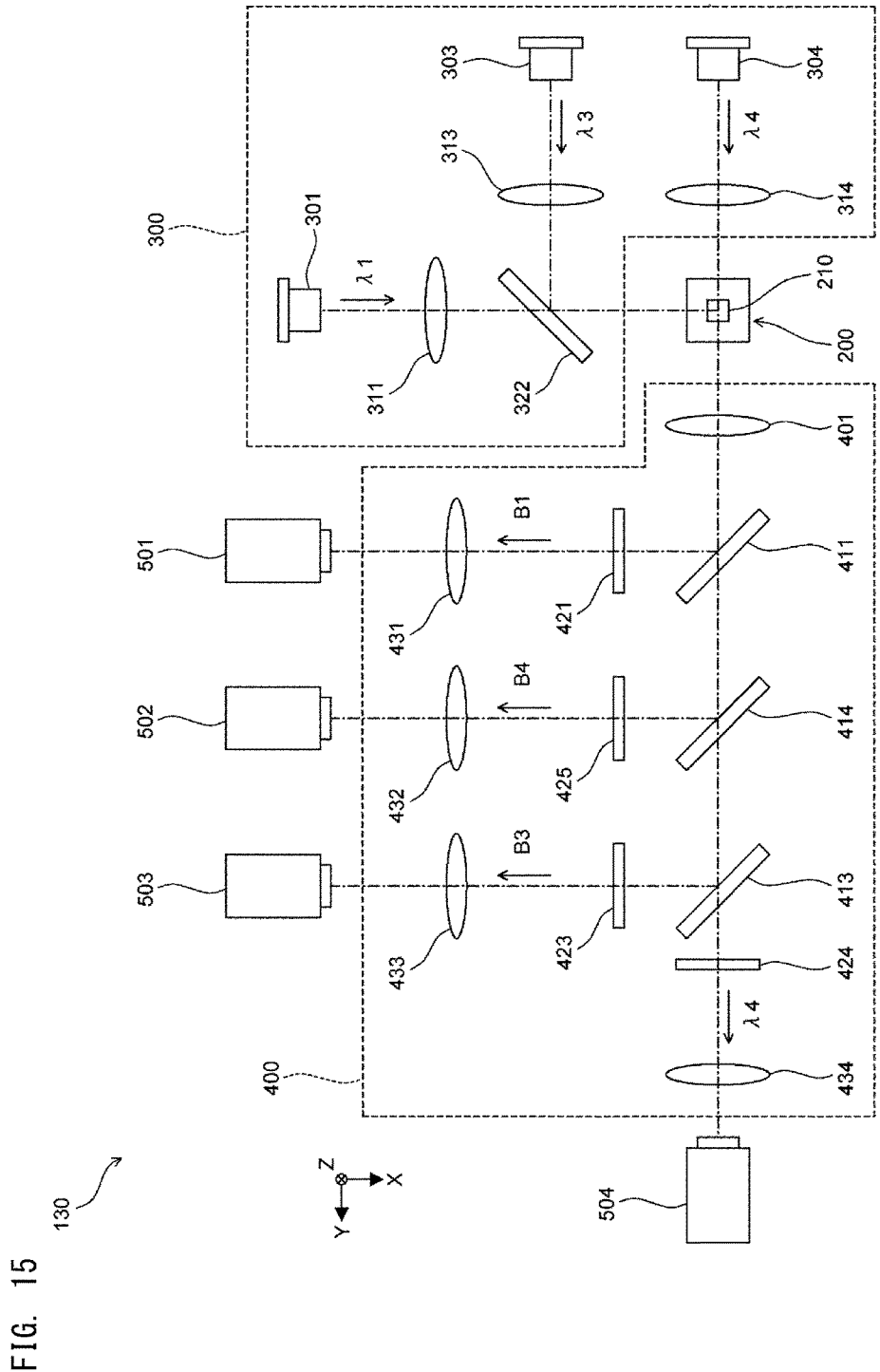
FIG. 15 shows a configuration of an optical detection unit according to Embodiment 3.

Compared with Embodiment 1, according to the apparatus configuration in Embodiment 3 as shown in FIG. 15, the light source 302, the condenser lens 312, and the dichroic mirror 321 are omitted, and filter members 414 and 425 are provided instead of the filter members 412 and 422, in the optical detection unit 130 shown in FIG. 6. Among the lights that have passed through the filter member 411, the filter member 414 reflects the light having the wavelength band B4 and allows light other than the light having the wavelength band B4 to pass therethrough. Of the light reflected by the filter member 414, the filter member 425 allows only the light having the wavelength band B4 to pass therethrough, and blocks light other than the light having the wavelength band B4. In this manner, the filter members 414 and 425 are each configured to be able to separate only the fluorescence having the wavelength band B4, among the lights generated at the flow cell 200. The light receiver 502 takes an image of low intensity fluorescence having the wavelength band B4.

Also in Embodiment 3, as in Embodiment 1, high intensity fluorescence and low intensity fluorescence are separately generated, whereby a high intensity fluorescence image and a low intensity fluorescence image can be obtained. Accordingly, as in Embodiment 1, on the basis of the high intensity fluorescence image and the low intensity fluorescence image, NF-κB having diverse distribution and amount in the cell can be accurately analyzed.

Embodiment 4

In Embodiment 4, among the steps of the cell information obtaining method shown in FIG. 1, only some procedures in steps S1 and S2 are different from those in Embodiment 1. In the following, the procedures different from those in Embodiment 1 will be described.

Figure 16:
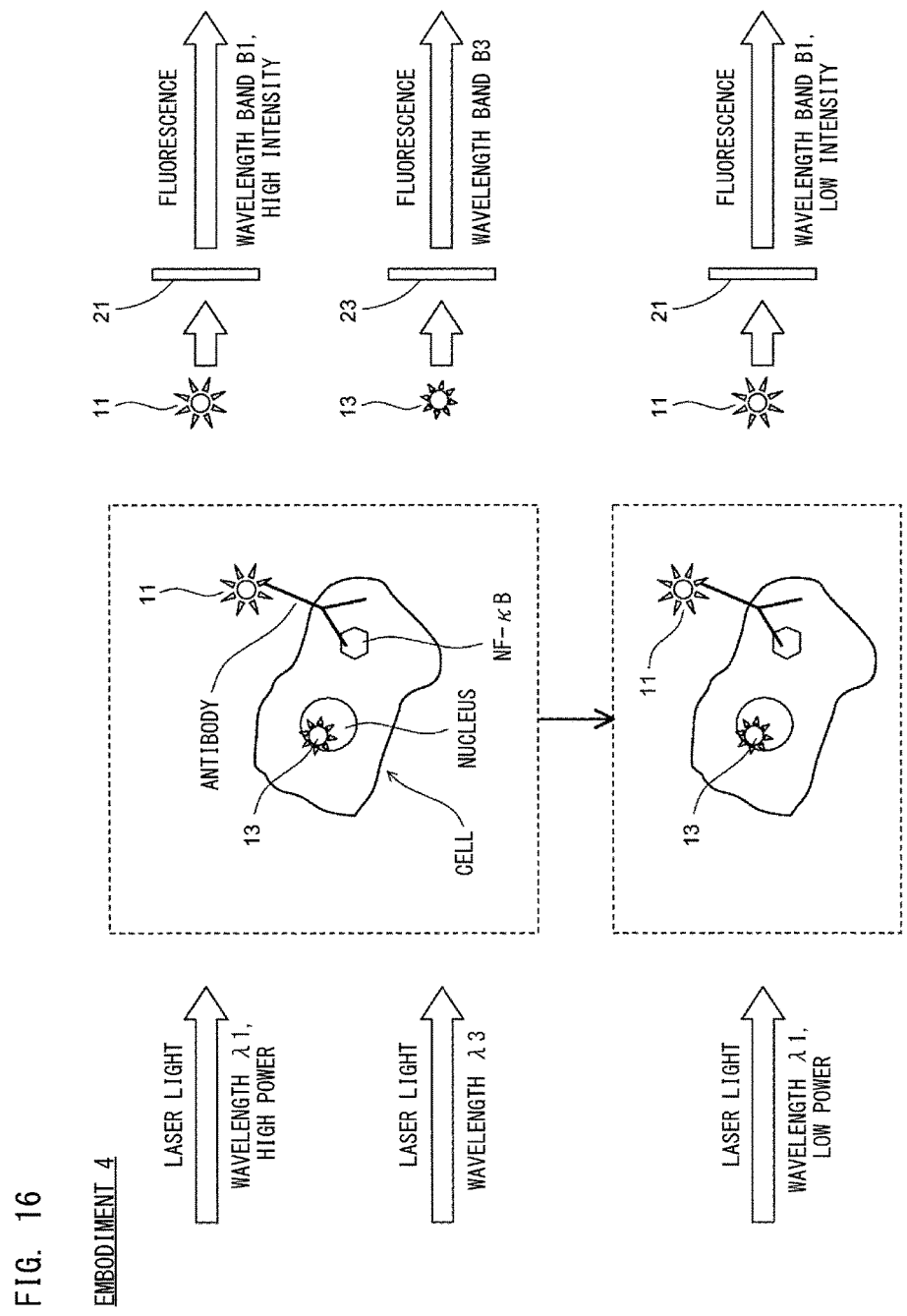
FIG. 16 shows the outline of how to obtain fluorescence according to Embodiment 4.

In step S1, as shown in FIG. 16, NF-κB contained in each cell is labeled with only the fluorescent substance 11 as used in Embodiment 1. In step S2, a sample containing the cells labeled with the fluorescent substances 11 and 13 is caused to flow in the flow cell. Lights respectively having the wavelengths λ1 and λ3 are applied to each cell flowing in the flow cell, whereby fluorescences are generated from the fluorescent substances 11 and 13, respectively. At this time, the light having the wavelength λ1 is applied at a high power to the cell, and thus, the fluorescence having the wavelength band B1 and having passed through the filter member 21 has a high intensity as in Embodiment 1. Further, this cell is moved in the flow cell, and light having the wavelength λ1 is applied to this moved cell, whereby fluorescence is generated from the fluorescent substance 11. At this time, the light having the wavelength λ1 is applied at a low power to the cell. Accordingly, fluorescence having the wavelength band B1 having passed through the filter member 21 has a low intensity.

Figure 17:
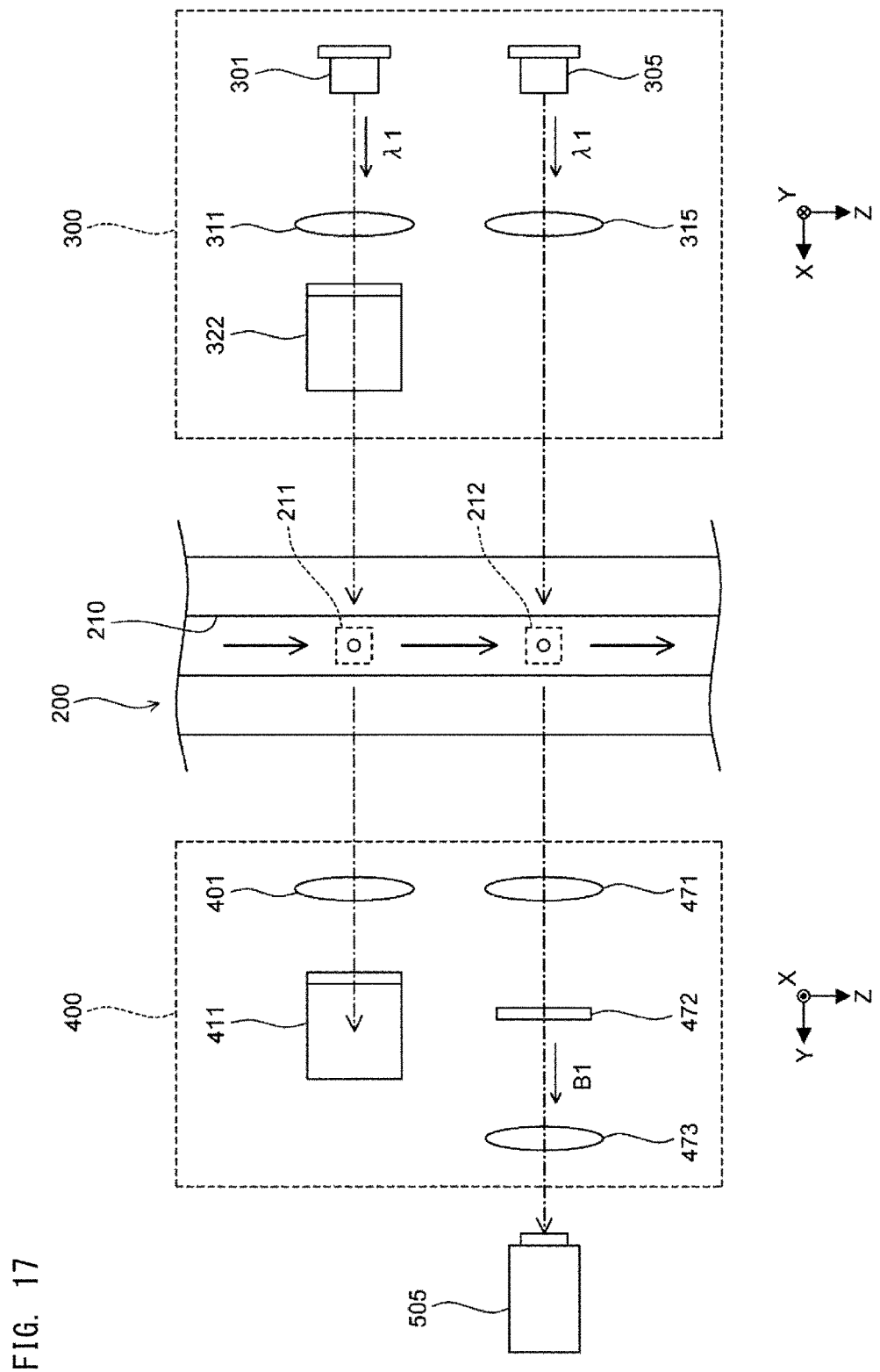
FIG. 17 shows a configuration of an optical detection unit according to Embodiment 4.

Compared with Embodiment 1, according to the apparatus configuration in Embodiment 4, the light source 302, the condenser lens 312, the dichroic mirror 321, the filter members 412 and 422, the condenser lens 432, and the light receiver 502 are omitted in the optical detection unit 130 shown in FIG. 6. Further, compared with Embodiment 1, according to the apparatus configuration in Embodiment 4 as shown in FIG. 17, a light source 305 and a condenser lens 315 are added to the light application unit 300, and a condenser lens 471, a filter member 472, and a condenser lens 473 are added to the light condensing unit 400. Further, compared with Embodiment 1, according to the apparatus configuration in Embodiment 4, a light receiver 505 is added.

FIG. 17 is a view at the time when the optical detection unit 130 is viewed in a direction parallel to the XY plane. For convenience, FIG. 17 shows the light application unit 300 viewed in the Y-axis positive direction, and the light condensing unit 400 and the light receiver 505 viewed in the X-axis negative direction.

Light having the wavelength λ1 and emitted from the light source 301 is applied to a position 211 in the flow pass 210 of the flow cell 200. The light source 305 has the same configuration as the light source 301, and emits light at a lower power than the light source 301. The condenser lens 315 condenses the light emitted from the light source 305, onto the position 212 located to the Z-axis positive side relative to the position 211 in the flow pass 210. The condenser lens 471 condenses fluorescence generated at the position 212. Of the light condensed by the condenser lens 471, the filter member 472 allows only light having the wavelength band B1 to pass therethrough. The light receiver 505 receives low intensity light having the wavelength band B1 and condensed by the condenser lens 473, and outputs, as an image pickup signal, image information based on the received light.

A time period T in which a cell is moved from the position 211 to the position 212 is obtained in advance. Thus, when the time period T elapses after a light based on a certain cell has been received by the light receiver 501, the light based on the same cell is received by the light receiver 505. Therefore, an image obtained on the basis of the light receiver 501 can be associated with an image obtained on the basis of the light receiver 505, as images obtained from the same cell.

Also in Embodiment 4, as in Embodiment 1, high intensity fluorescence and low intensity fluorescence are separately generated, whereby a high intensity fluorescence image and a low intensity fluorescence image can be obtained. Accordingly, as in Embodiment 1, on the basis of the high intensity fluorescence image and the low intensity fluorescence image, NF-κB having diverse distribution and amount in the cell can be accurately analyzed.

Embodiment 5

In Embodiment 5, among the steps of the cell information obtaining method shown in FIG. 1, only some procedures in step S2 are different from those in Embodiment 1. In the following, the procedures different from those in Embodiment 1 will be described.

Figure 18:
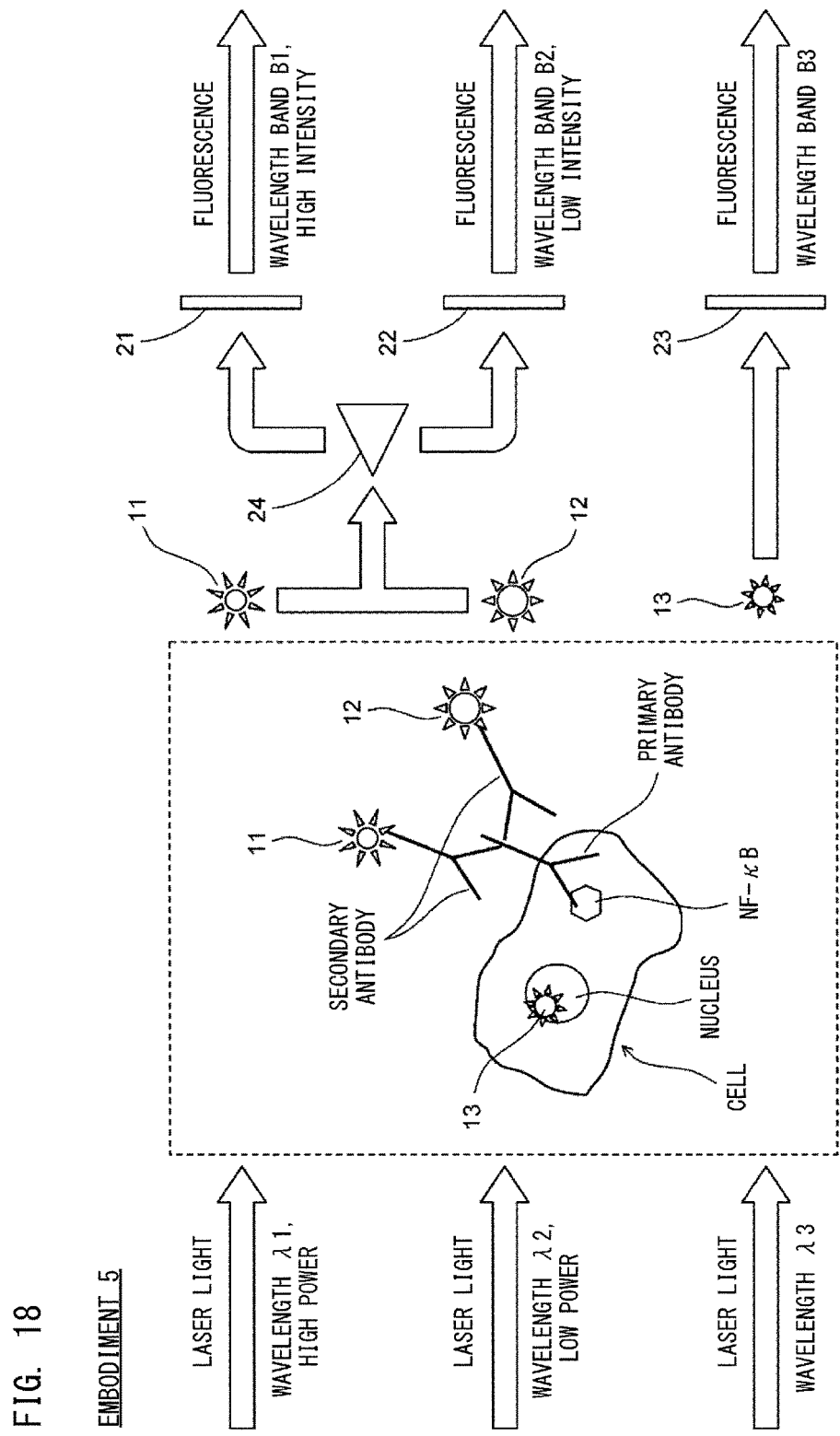
FIG. 18 shows the outline of how to obtain fluorescence according to Embodiment 5.

In step S2, as shown in FIG. 18, a sample containing the cells labeled with the fluorescent substances 11 to 13 is caused to flow in the flow cell. Lights respectively having the wavelengths λ1 to λ3 are applied to each cell flowing in the flow cell, whereby fluorescences are generated from the fluorescent substances 11 to 13, respectively. The fluorescences generated from the fluorescent substances 11 and 12 are combined to be incident onto a filter member 24. The filter member 24 is implemented by a prism. Due to the difference in the wavelength band, the combined fluorescence generated from the fluorescent substances 11 and 12 is split by the filter member 24 into a fluorescence having the wavelength band B1 and a fluorescence having the wavelength band B2. Here, as in Embodiment 1, the light having the wavelength λ1 is applied at a high power to the cell, and the light having the wavelength λ2 is applied at a low power to the cell. As a result, as in Embodiment 1, the fluorescence having the wavelength band B1 and having passed through the filter member 21 has a high intensity, and the fluorescence having the wavelength band B2 and having passed through the filter member 22 has a low intensity.

It should be noted that fluorescences generated from the fluorescent substances 11 to 13 may be combined to be incident onto the filter member 24, and then, due to the difference in the wavelength band, the combined fluorescence may be split by the filter member 24 into fluorescences having the wavelength bands B1 to B3, respectively. In the example shown here, the filter member 24 is used in the configuration of Embodiment 1, but the filter member 24 may be used in the configurations of Embodiments 2 to 4.

Figure 19:
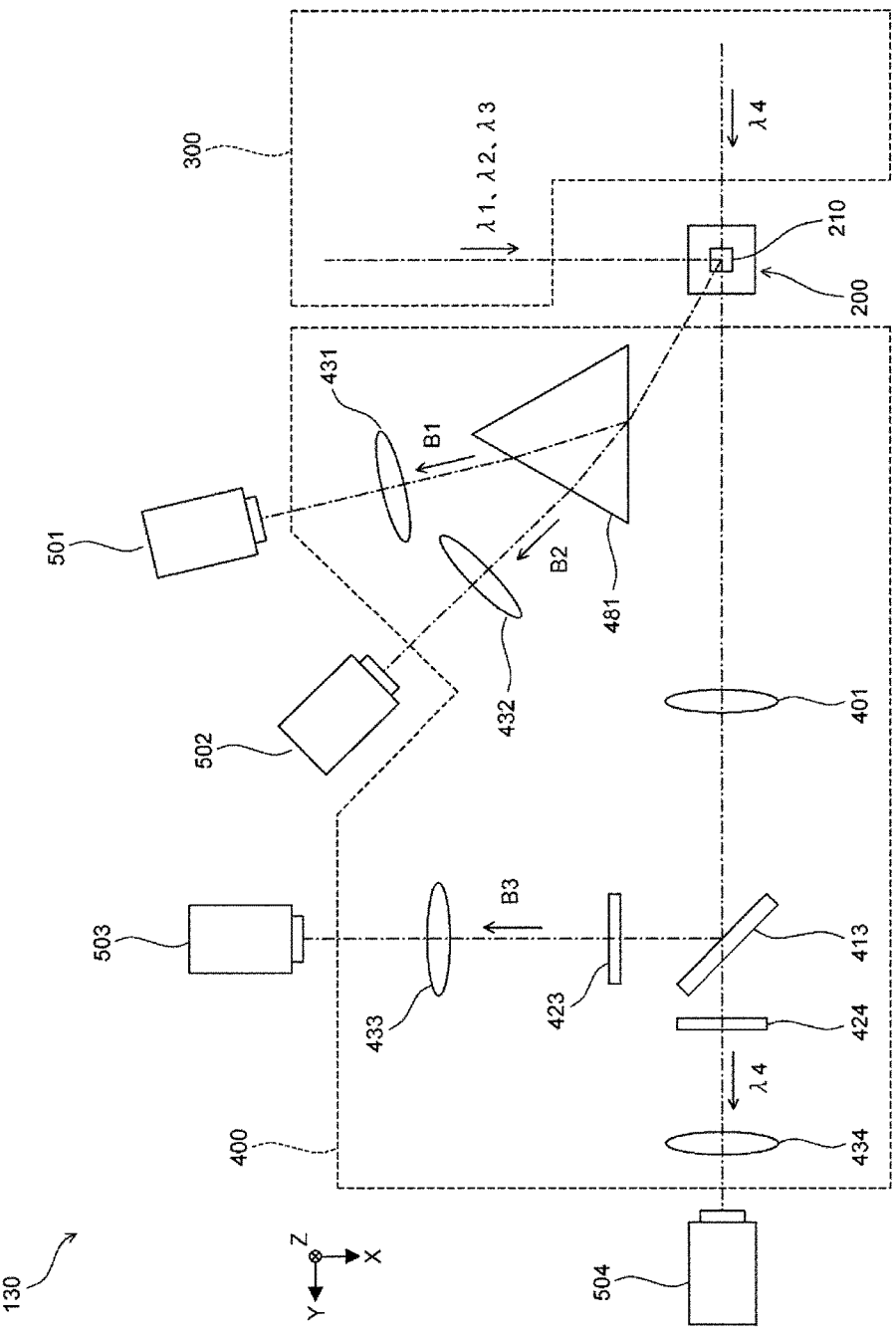
FIG. 19 shows a configuration of an optical detection unit according to Embodiment 5.

Compared with Embodiment 1, according to the apparatus configuration in Embodiment 5 as shown in FIG. 19, in the optical detection unit 130 shown in FIG. 6, the filter members 411, 412, 421, and 422 are omitted, and a filter member 481 is added to the light condensing unit 400. The filter member 481 is implemented by a prism.

Fluorescences generated from a sample flowing in the flow cell 200 are incident on the filter member 481. The fluorescences incident on the filter member 481 go out from the filter member 481 at different angles according to their fluorescence wavelengths, respectively. The condenser lens 431 and the light receiver 501 are disposed in a direction that corresponds to the fluorescence having the wavelength band B1, of the fluorescences going out from the filter member 481. Accordingly, the light receiver 501 can take an image of high intensity fluorescence having the wavelength band B1. The condenser lens 432 and the light receiver 502 are disposed in a direction that corresponds to the fluorescence having the wavelength band B2, of the fluorescences going out from the filter member 481. Accordingly, the light receiver 502 can take an image of low intensity fluorescence having the wavelength band B2.

Also in Embodiment 5, as in Embodiment 1, high intensity fluorescence and low intensity fluorescence are separately generated, whereby a high intensity fluorescence image and a low intensity fluorescence image can be obtained. Accordingly, as in Embodiment 1, on the basis of the high intensity fluorescence image and the low intensity fluorescence image, NF-κB having diverse distribution and amount in the cell can be accurately analyzed.

Embodiment 6

In Embodiment 6, a test substance contained in a cell is brought into contact with a substrate, thereby causing a fluorescent substance to be generated; then, light is applied to the generated fluorescent substance; and then, on the basis of fluorescence that has been generated from the fluorescent substance upon the application of the light, the localization state of the test substance is identified. In Embodiment 6, the test substance is cytoplasm. The substrate includes a cleavage site at which the substrate is cleaved upon contact with the test substance, and when the substrate is cleaved at the cleavage site, the substrate generates a fluorescent substance. More specifically, when the substrate comes into contact with the cytoplasm being the test substance, the substrate is cleaved by an enzyme present in the cytoplasm. In Embodiment 6, localization of the cytoplasm is judged on the basis of fluorescence from the fluorescent substance labeling the cytoplasm. It should be noted that the test substance may be, for example, a substance other than cytoplasm contained in a cell, such as protein in cytoplasm, organelle, cell membrane, or the like.

In Embodiment 6, among the steps of the cell information obtaining method shown in FIG. 1, some procedures in step S1 are different from those in Embodiment 3. In the following, the procedures different from those in Embodiment 3 will be described.

Figure 20:
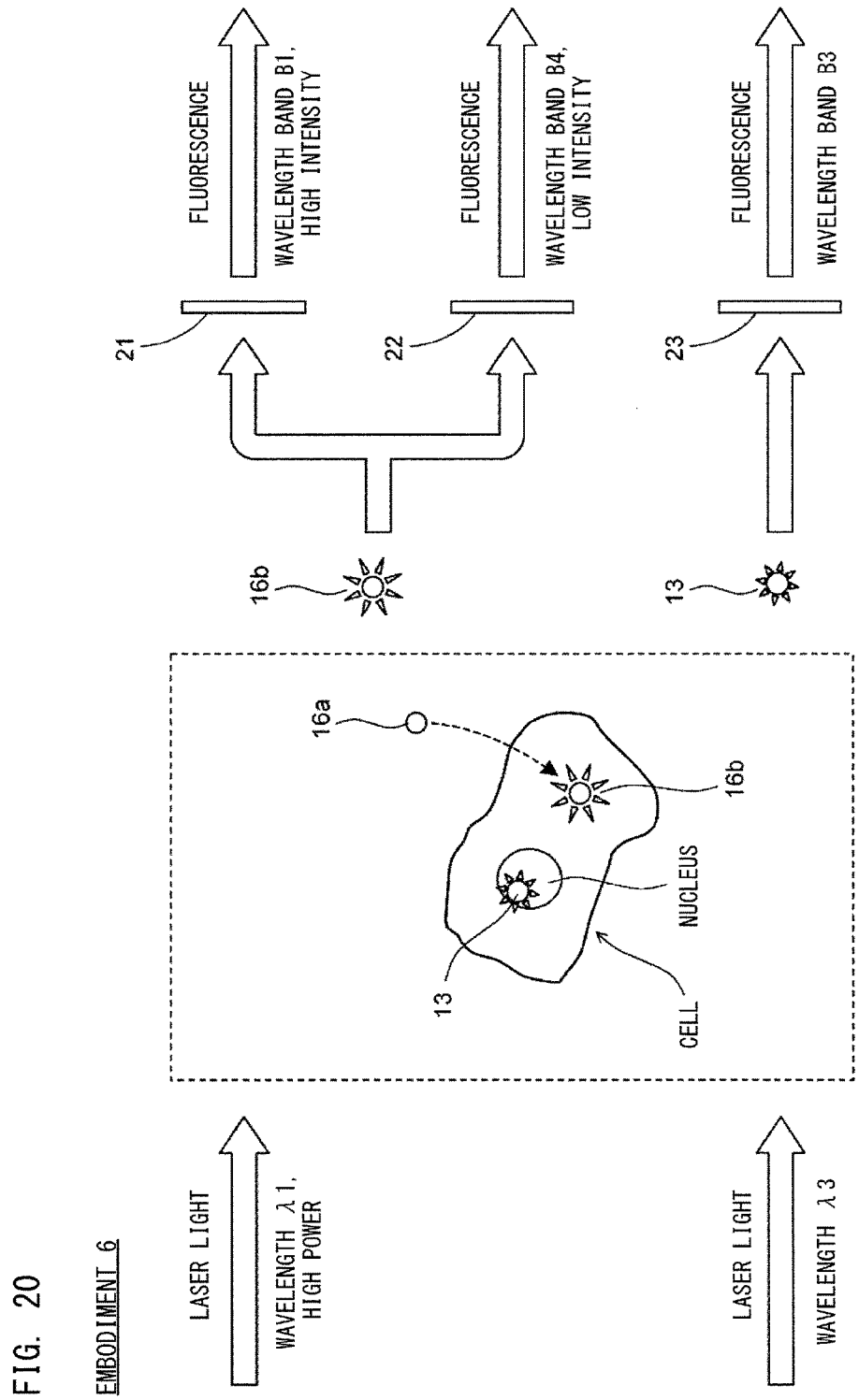
FIG. 20 shows the outline of how to obtain fluorescence according to Embodiment 6.

In step S1, as shown in FIG. 20, the cell and a substrate 16a are mixed together. The substrate 16a generates a fluorescent substance 16b when being hydrolyzed with esterase contained in the cytoplasm. When the cell and the substrate 16a are mixed together, the substrate 16a having passed through the cell membrane comes into contact with the cytoplasm, thereby being hydrolyzed with the esterase contained in the cytoplasm, to generate the fluorescent substance 16b. Accordingly, the cytoplasm is labeled with the fluorescent substance 16b.

Subsequently, the processes of step S2 and thereafter will be performed as in Embodiment 3. That is, in step S2, a sample containing the cells labeled with the fluorescent substance 16b is caused to flow in the flow cell. Then, as shown in FIG. 20, lights respectively having the wavelengths λ1 and λ3 are applied to each cell flowing in the flow cell, whereby fluorescences are generated from the fluorescent substances 16b and 13, respectively. Then, as shown in FIG. 20, the fluorescence generated from the fluorescent substance 16b is divided into two, one of which is caused to pass through the filter member 21, and the other of which is caused to pass through the filter member 22. As a result, as in Embodiment 3, the fluorescence having the wavelength band B1 and having passed through the filter member 21 has a high intensity, and the fluorescence having the wavelength band B4 and having passed through the filter member 22 has a low intensity. It should be noted that the apparatus according to Embodiment 6 has the same configuration as that in Embodiment 3.

Also in Embodiment 6, as in Embodiment 3, two fluorescences respectively having different intensities are generated, whereby a high intensity fluorescence image and a low intensity fluorescence image can be obtained. Accordingly, on the basis of the high intensity fluorescence image and the low intensity fluorescence image, localization of the cytoplasm can be accurately identified. Thus, if localization of the cytoplasm can be accurately identified, the range of the cytoplasm can be precisely defined. Accordingly, for example, if the range of the cytoplasm is combined with another analysis, further detailed analysis is enabled. Moreover, for example, the range of the cytoplasm can be utilized in study of cells and the like.

Examination of Embodiment 6

Next, examination of Embodiment 6 performed by the inventor will be described.

1. Preparation

As the cells, human cardiac microvascular endothelial cells (HMVEC-C) (Lonza Cat No. CC-7030, Lot No. 0000296500 (P4)) were obtained. As the cytoplasm labeling reagent, Cell Explorer Fixable Live Cell Tracking Kit *Green Fluorescence* (Cosmo Bio 22621) was obtained. The cytoplasm labeling reagent contains a substance that corresponds to the substrate 16a shown in FIG. 20. The cytoplasm labeling reagent is hydrophobic. By passing through the cell membrane and being hydrolyzed with esterase in the cell, the cytoplasm labeling reagent generates a fluorescent substance. The fluorescent substance generated here corresponds to the fluorescent substance 16b shown in FIG. 20. As the nucleus staining dye, Cellstain Hoechst 33342 solution (DOjinDO 11342) was obtained. Other than these, EGM-2MV Medium (Lonza Cat No. CC-3202), EGM-2MV SingleQuots Kit (Lonza Cat No. CC-3202), PBS pH7.4 (GIBCO Cat No. 10010-023), BSA (LAMPIRE Cat No. 7500805), PFA (WAKO Cat No. 160-16061), and TritonX100 (Nacalai Tesque Cat No. 35501-15) were obtained.

2. Reagent Preparation

EGM-2MV SingleQuots Kit was added to 500 mL of EGM-2MV Medium, to create a culture medium. Paraformaldehyde was dissolved in pH12 PBS so as to have a final concentration of 8% w/v, and then the pH was adjusted to 7.4. 1.5 g of BSA was added to and dissolved in PBS, and PBS was additionally added thereto to obtain 50 mL, whereby 3% BSA/PBS was prepared. 0.5 g of BSA was added to and dissolved in PBS, and PBS was additionally added thereto to obtain 50 mL, whereby 1% BSA/PBS was prepared. TritonX100 was adjusted with PBS to have a final concentration of 0.1% w/v. 100 μL of DMSO was added to a Track kit Green vial to create a 1000×Track kit Green stock solution, and by adding a 1/1000 amount thereof to an Assay buffer of the Kit, a Track kit working solution was prepared.

3. Procedure

HMVEC-C cells were cultured in the EGM-2MV culture medium in accordance with a manufacturer-recommended protocol. Cells within six passages after the purchase thereof were used in this examination. The shelf life of the culture medium was set to three weeks. After the cell culture became 70% confluent, the culture medium was removed with an electric pipette, with about 3 mL of the culture medium left, and the cells were detached with a scraper. 3 μL of the Track kit working solution was added to the collected 3 mL suspension, and the resultant mixture was left still for 30 minutes in an 37° C. $CO^2$ incubator. After the mixture was left still for 30 minutes, the mixture was centrifuged at 1000 rpm for 3 minutes at room temperature. The cell pellet was washed with 5 mL of PBS three times. The supernatant was removed and 50 μL of 1% BSA/PBS was added.

4. Detection by Flow Cytometer

As a flow cytometer that can obtain fluorescence images, ImageStreamX Mark II Imaging Flow Cytometer (Merck Millipore) was used. A sample prepared in accordance with the procedure 3 above was caused to flow in the flow cell of the flow cytometer. Laser lights respectively having wavelengths of 488 nm and 405 nm were applied to the sample flowing in the flow cell. The laser lights having the wavelengths of 488 nm and 405 nm correspond to the laser lights having the wavelengths λ1 and λ3 shown in FIG. 20, respectively. The emission powers of the laser lights having the wavelengths of 488 nm and 405 nm were set to 50 mW and 20 mW, respectively. As a result of the application of the laser light having the wavelength of 488 nm to the fluorescent dye labeling the cytoplasm, fluorescence was generated. As a result of the application of the laser light having the wavelength of 405 nm to the nucleus staining dye, fluorescence was generated.

In the flow cytometer above, an image of the fluorescence generated due to the laser light having the wavelength of 488 nm was taken via a filter member having a transmission wavelength band of 480 nm to 560 nm, whereby a high intensity fluorescence image was obtained. An image of the fluorescence generated due to the laser light having the wavelength of 488 nm was taken via a filter member having a transmission wavelength band of 560 nm to 595 nm, whereby a low intensity fluorescence image was obtained. An image of the fluorescence generated due to the laser light having the wavelength of 405 nm was taken via a filter member having a transmission wavelength band of 420 nm to 505 nm, and a fluorescence image corresponding to the nucleus was obtained. Furthermore, a laser light whose wavelength was set between 420 nm to 480 nm was applied to the sample flowing in the flow cell. An image of the light obtained as a result of this laser light having passed through the cell was taken via the filter member having a transmission wavelength band of 420 nm to 480 nm, whereby a bright field image was obtained. In the flow cytometer above, light having unnecessary wavelength bands is removed by a filter member or the like such that light having a target wavelength band is appropriately incident on the light receiver.

Figure 21:
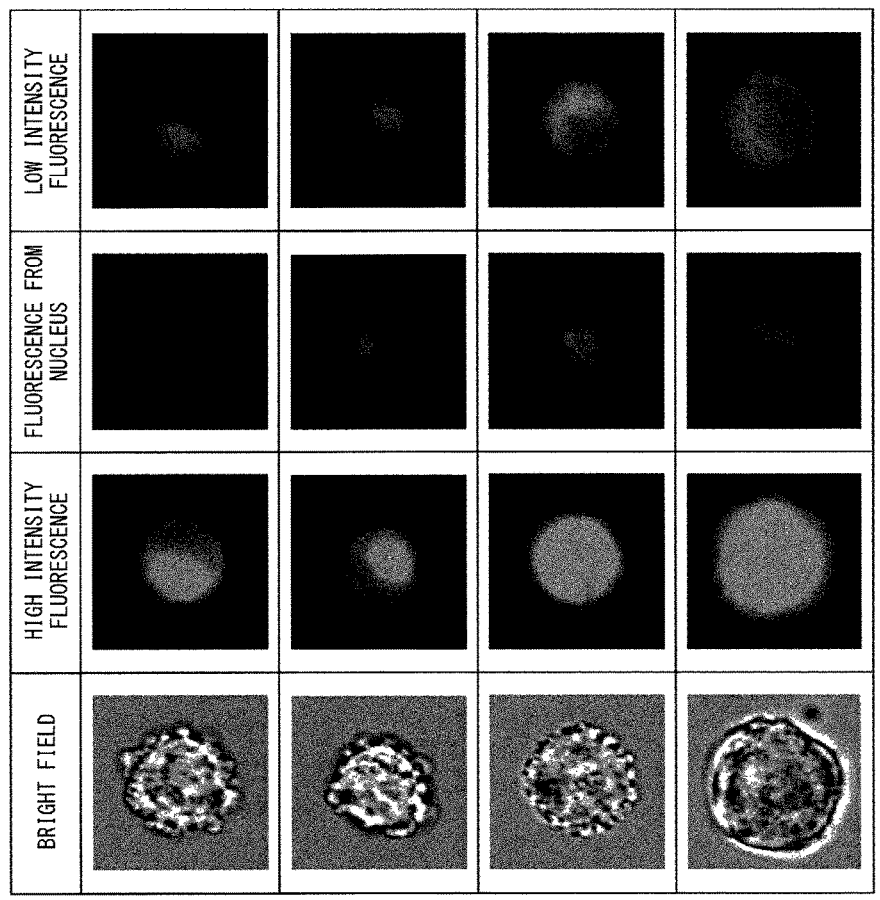
FIG. 21 shows images obtained in an examination according to Embodiment 6.
Figure 23A:
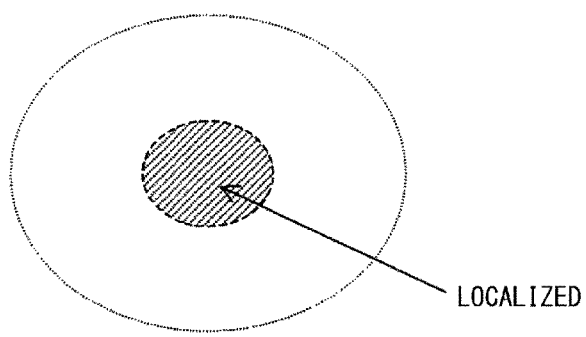
FIGS. 23A, 23B and 23C are schematic diagrams for explaining the problem to be solved by the present invention.
Figure 23B:
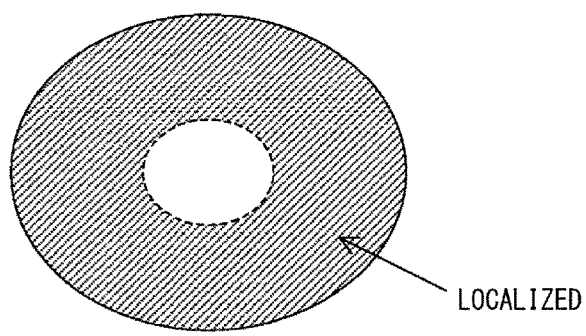
Figure 23C:
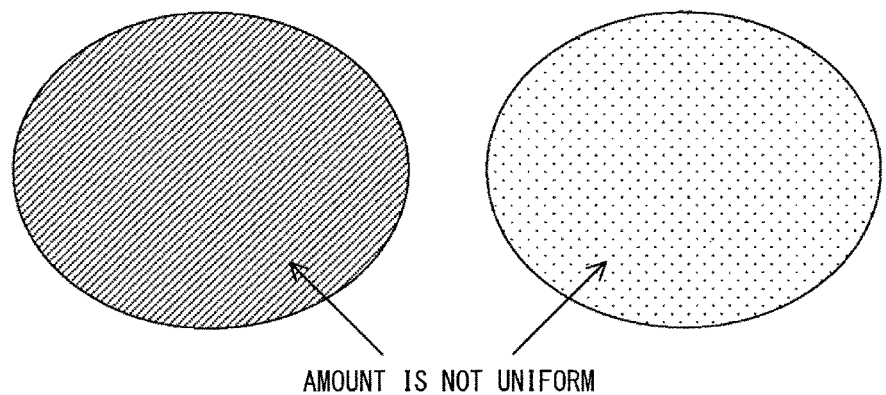

With reference to FIG. 21, images obtained through the detection above will be described.

"BRIGHT FIELD" indicates a bright field image of a cell. "HIGH INTENSITY FLUORESCENCE" and "LOW INTENSITY FLUORESCENCE" respectively correspond to an image based on high intensity fluorescence generated from the fluorescent dye labeling the cytoplasm, and an image based on low intensity fluorescence generated from the fluorescent dye labeling the cytoplasm. "FLUORESCENCE FROM NUCLEUS" corresponds to an image based on fluorescence generated from the nucleus staining dye that stains the nucleus. The four images arranged along the horizontal direction are images obtained from one cell. The images other than the bright field image are gray scale expressions of the obtained color images, made for convenience. In the images other than the bright field image, the white portion indicates that the intensity of the fluorescence is high.

In the case of the cell at the top row and the cell in the second row from the top, in the image based on the low intensity fluorescence, the intensity is too low. Thus, localization of the cytoplasm is not clear. On the other hand, in the case of the image based on the high intensity fluorescence, the intensity is appropriate. Thus, it is possible to accurately identify localization of the cytoplasm. In the case of the cell in the lowest row and the cell in the second lowest row, in the image based on the high intensity fluorescence, the intensity is too high. Thus, localization of the cytoplasm is difficult to be identified. On the other hand, in the case of the image based on the low intensity fluorescence, the intensity is appropriate. Thus, localization of the cytoplasm can be accurately identified.

As described above, this examination shows that localization of the cytoplasm can be identified on the basis of the two fluorescence images respectively having different intensities as in Embodiment 6. Thus, according to Embodiment 6, if fluorescence generated from one kind of fluorescent dye labeling the cytoplasm is allowed to pass through the filter members 21 and 22 which respectively allow fluorescences having different wavelength bands to pass therethrough, and two fluorescence images can be obtained, accordingly, it is possible to accurately identify localization of the cytoplasm through a single measurement for one cell.

Embodiment 7

In Embodiment 7, a test substance contained in a cell is brought into contact with two kinds of substrates, thereby causing two kinds of fluorescent substances to be generated; then light is applied to the generated two kinds of fluorescent substances; and then, on the basis of the fluorescences that have been generated from the two kinds of fluorescent substances upon the application of the light, the localization state of the test substance is identified. That is, in Embodiment 7, not by using one light as in Embodiment 6, but by using lights respectively having different wavelengths, fluorescences respectively having different intensities are obtained. It should be noted that two kinds of fluorescent substances may be generated by bringing the test substance into contact with one kind of substrate.

In Embodiment 7, among the step of the cell information obtaining method shown in FIG. 1, only some procedures in steps S1 and S2 are different from those in Embodiment 6. In the following, the procedures different from those in Embodiment 6 will be described.

In step S1, as shown in FIG. 22, the cell and substrates 17a and 18a are mixed together. The substrates 17a and 18a generate fluorescent substances 17b and 18b respectively when being hydrolyzed with esterase contained in the cytoplasm. The fluorescent substances 17b and 18b are configured to excite fluorescences having different wavelength bands from each other when being irradiated with lights having the wavelengths $\lambda 1$ and $\lambda 2$, respectively. When the cell and the substrates 17a and 18a are mixed together, the substrates 17a and 18a having passed through the cell membrane come into contact with the cytoplasm, thereby being hydrolyzed with esterase contained in the cytoplasm, to generate the fluorescent substances 17b and 18b. Accordingly, the cytoplasm is labeled with the fluorescent substances 17b and 18b.

In step S2, a sample containing the cells labeled with the fluorescent substances 17b and 18b are caused to flow in the flow cell. Then, as shown in FIG. 22, lights respectively having the wavelengths $\lambda 1$, $\lambda 2$, and $\lambda 3$ are applied to each cell flowing in the flow cell, whereby fluorescences are generated from the fluorescent substances 17b, 18b, and 13, respectively. At this time, the laser light having the wavelength $\lambda 1$ is applied to the cell at a high power, and the laser light having the wavelength $\lambda 2$ is applied to the cell at a low power. The fluorescence generated from the fluorescent substance 17b is passed through the filter member 21, thereby becoming fluorescence having the wavelength band B1. The fluorescence generated from the fluorescent substance 18b is passed through the filter member 22, thereby becoming fluorescence having the wavelength band B2. As a result, the fluorescence having the wavelength band B1 and having passed through the filter member 21 has a high intensity, and the fluorescence having the wavelength band B2 and having passed through the filter member 22 has a low intensity. It should be noted that the apparatus according to Embodiment 7 has the same configuration as that in Embodiment 1.

Also in Embodiment 7, as in Embodiment 6, two fluorescences respectively having different intensities are generated, whereby a high intensity fluorescence image and a low intensity fluorescence image can be obtained. Accordingly, as in Embodiment 6, on the basis of the high intensity fluorescence image and the low intensity fluorescence image, localization of the cytoplasm can be accurately identified.

What is claimed is:

1. A cell information obtaining method comprising:
causing a plurality of fluorescent substances, each having different fluorescence wavelengths from each other to be bound to a test substance contained in a cell, wherein the test substance is the same for each of the plurality of fluorescent substances;
applying light to the cell to cause fluorescences having different wavelengths and intensities to be generated from the plurality of fluorescent substances; and
obtaining a first fluorescence information and a second fluorescence information on the basis of the generated fluorescences.

2. The cell information obtaining method of claim 1, wherein a distribution state of the test substance in the cell is identified on the basis of the first fluorescence information and the second fluorescence information.

3. The cell information obtaining method of claim 1, wherein a localization state of the test substance in the cell is identified on the basis of the first fluorescence information and the second fluorescence information.

4. The cell information obtaining method of claim 1, wherein whether the test substance is nuclearly localized or cytoplasmically localized is identified on the basis of the first fluorescence information and the second fluorescence information.

5. The cell information obtaining method of claim 1, wherein wavelengths for excitation light for the plurality of fluorescent substances are different from each other.

6. The cell information obtaining method of claim 1, wherein first light and second light which has a lower intensity than that of the first light are applied to the cell.

7. The cell information obtaining method of claim 1, wherein wavelengths and intensities of fluorescences generated from the plurality of fluorescent substances by being irradiated with light having the same wavelength are different from each other.

8. The cell information obtaining method of claim 1, wherein the fluorescences generated from the plurality of fluorescent substances are separated into a first fluorescence and a second fluorescence which has a lower intensity than that of the first fluorescence.

9. A cell information obtaining method comprising:
causing a fluorescent substance to be bound to a test substance contained in a cell;
applying light to the cell to cause a fluorescence to be generated from the fluorescent substance;
obtaining, from the generated fluorescence, a plurality of fluorescences having different wavelengths and intensities;
obtaining a first fluorescence information and a second fluorescence information on the basis of the obtained fluorescences; and
identifying a localization state of the test substance in the cell on the basis of the first fluorescence information and the second fluorescence information.

10. The cell information obtaining method of claim 9, wherein the fluorescences generated from the fluorescent substance are separated into a first fluorescence and a second fluorescence which has a lower intensity than that of the first fluorescence.

11. The cell information obtaining method of claim 1, further comprising:

obtaining a first fluorescence image of a fluorescence having a first wavelength and having been generated from the cell irradiated with first light, and obtaining a second fluorescence image of a fluorescence having a second wavelength and having been generated from the cell irradiated with second light which has a lower intensity than that of the first light.

12. The cell information obtaining method of claim 1, wherein a sample containing the cell is caused to flow in a flow cell, and light is applied to the cell flowing in the flow cell, to cause the fluorescence to be generated.

13. The cell information obtaining method of claim 3, wherein the identification of the localization state of the test substance includes calculation of a proportion of a localization amount of the test substance in an analysis target site in the cell relative to a localization amount of the test substance in an entirety of the cell.

14. The cell information obtaining method of claim 3, wherein the identification of the localization state of the test substance is performed on the basis of, among the first fluorescence information and the second fluorescence information obtained from the plurality of fluorescences having different intensities, fluorescence information obtained from a fluorescence whose intensity is included in a predetermined range, where the predetermined range is between a condition in which the first or second fluorescence information lacks sufficient signal intensity from the cell to distinguish regions of the cell, and a condition in which the signal intensity of the first or second fluorescence information from the cell is spatially indistinguishable in the cell.

15. The cell information obtaining method of claim 3, wherein the identification of the localization state of the test substance in the cell is performed on the basis of, among the first fluorescence information and the second fluorescence information obtained from the plurality of fluorescences having different signal intensities, fluorescence information in which a difference between the signal intensity of the fluorescence at an analysis target site in the cell and the signal intensity of the fluorescence in a portion other than the analysis target site, of the cell is greater than a predetermined signal intensity level threshold.

16. The cell information obtaining method of claim 1, wherein the test substance is a protein, mRNA, microRNA, cytoplasm, organelle, or cell membrane.

17. The cell information obtaining method of claim 1, wherein a proportion or the number of cells in which the test substance is localized in a specific site among the cells contained in the sample is calculated on the basis of the first fluorescence information and the second fluorescence information.

18. A cell information obtaining apparatus comprising:
a light application unit configured to apply light to a cell containing a test substance to which a plurality of fluorescent substances, each having different fluorescence wavelengths from each other are bound, thereby to cause fluorescences having different wavelengths and intensities to be generated from the plurality of fluorescent substances, wherein the test substance is the same for each of the plurality of fluorescent substances;
a light receiver configured to receive the fluorescences generated from the plurality of fluorescent substances; and
an obtaining section configured to obtain a first fluorescence information and a second fluorescence information on the basis of the fluorescences having different intensities.

19. The cell information obtaining apparatus of claim 18, wherein
the light application unit includes:
a first light source configured to apply first light; and
a second light source configured to apply second light having a wavelength different from that of the first light and having a lower intensity than that of the first light.

* * * * *